(12) United States Patent
Dean et al.

(10) Patent No.: US 7,297,694 B2
(45) Date of Patent: Nov. 20, 2007

(54) PYRIDYLFURANS AND PYRROLES AS RAF KINASE INHIBITORS

(75) Inventors: David Kenneth Dean, Harlow (GB); Antoinette Naylor, Harlow (GB); Andrew Kenneth Takle, Harlow (GB); David Matthew Wilson, Harlow (GB)

(73) Assignee: SmithKline Beechum P.L.C., Middlesex (GB)

( * ) Notice: Subject to any disclaimer, the term of this patent is extended or adjusted under 35 U.S.C. 154(b) by 483 days.

(21) Appl. No.: 10/488,576

(22) PCT Filed: Sep. 5, 2002

(86) PCT No.: PCT/EP02/09945

§ 371 (c)(1),
(2), (4) Date: Mar. 4, 2004

(87) PCT Pub. No.: WO03/022833

PCT Pub. Date: Mar. 20, 2003

(65) Prior Publication Data

US 2004/0254186 A1 Dec. 16, 2004

(30) Foreign Application Priority Data

Sep. 5, 2001 (GB) ................................. 0121488.1

(51) Int. Cl.
*A61K 31/506* (2006.01)
*A61K 31/443* (2006.01)
*A61K 31/4439* (2006.01)
*C07D 401/04* (2006.01)
*C07D 405/04* (2006.01)
*C07D 405/14* (2006.01)
*C07D 407/14* (2006.01)

(52) U.S. Cl. ............................. 514/235.8; 514/252.18; 514/272; 514/274; 514/318; 514/336; 514/343; 544/123; 544/295; 544/315; 544/331; 546/194; 546/276.4; 546/283.4

(58) Field of Classification Search ................. 546/194, 546/276.4, 283.4; 544/123, 295, 315, 331, 544/316; 514/235.8, 252.18, 272, 274, 318, 514/336, 343
See application file for complete search history.

(56) References Cited

FOREIGN PATENT DOCUMENTS

| GB | 2 306 108 | 4/1997 |
|---|---|---|
| WO | WO 97/36587 | 10/1997 |
| WO | WO 00/64422 | 11/2000 |
| WO | WO 01/38324 | 5/2001 |
| WO | WO 01/66539 | 9/2001 |
| WO | WO 01/66540 | 9/2001 |
| WO | WO 02/24680 | 3/2002 |

OTHER PUBLICATIONS

De Laszlo et al., "Pyrroles and other heterocycles as inhibitors of p38 kinase", Bioorg. Med. Chem. Lett., vol. 8, 1998, pp. 2689-2694.
De Laszlo et al., "Potent, orally abosorbed glucagon receptor antagonists", Bioorg. Med. Chem. Lettl, vol. 9, 1999, pp. 641-646.
Liveton et al., "Design and Synthesis of Potent, Selective and Orally Bioavailable Tetrasubstituted Imidazole Inhibitors of p38 Mitogen-Activated Protein Kinase", J. Med. Chem., vol. 42, No. 12, 1999, pp. 2180-2190.
Kalmes et al., "Raf-1 is activated by the p38 mitogen-activated protein kinase inhibitor", Febs Letters, vol. 444, No. 1, 1999. pp. 71-74.
Wermuth, C.G. (ed.), "Chapter 13: Molecular Variations Based on Isosteric Replacements", *The Practice of Medicinal Chemistry*, pp. 204-237, Academic Press Ltd., Copyright (1996), XP-002190259.

Primary Examiner—Bernard Dentz
(74) Attorney, Agent, or Firm—Grace C. Hsu; Mary E. McCarthy; Cjarles M. Kinzig

(57) ABSTRACT

Compounds and their use as pharmaceuticals particularly as Raf kinase inhibitors for the treatment of neurotraumatic diseases, cancer, chronic neurodegeneration, pain, migraine and cardiac hypertrophy.

9 Claims, No Drawings

PYRIDYLFURANS AND PYRROLES AS RAF KINASE INHIBITORS

This application is a §371 national stage filing of PCT/EP02/09945 filed 5 Sep. 2002.

This invention relates to novel compounds and their use as pharmaceuticals, particularly as Raf kinase inhibitors for the treatment of neurotraumatic diseases, cancer, chronic neurodegeneration, pain, migraine and cardiac hypertrophy.

Raf protein kinases are key components of signal transduction pathways by which specific extracellular stimuli elicit precise cellular responses in mammalian cells. Activated cell surface receptors activate ras/rap proteins at the inner aspect of the plasma-membrane which in turn recruit and activate Raf proteins. Activated Raf proteins phosphorylate and activate the intracellular protein kinases MEK1 and MEK2. In turn, activated MEKs catalyse phosphorylation and activation of p42/p44 mitogen-activated protein kinase (MAPK). A variety of cytoplasmic and nuclear substrates of activated MAPK are known which directly or indirectly contribute to the cellular response to environmental change. Three distinct genes have been identified in mammals that encode Raf proteins; A-Raf, B-Raf and C-Raf (also known as Raf-1) and isoformnic variants that result from differential splicing of mRNA are known.

Inhibitors of Raf kinases have been suggested for use in disruption of tumor cell growth and hence in the treatment of cancers, e.g. histiocytic lymphoma, lung adenocarcinoma, small cell lung cancer and pancreatic and breast-carcinoma; also in the treatment and/or prophylaxis of disorders associated with neuronal degeneration resulting from ischemic events, including cerebral ischemia after cardiac arrest, stroke and multi-infarct dementia and also after cerebral ischemic events such as those resulting from head injury, surgery and/or during childbirth; also in chronic neurodegeneration such as Alzheimer's disease and Parkinson's disease; also in the treatment of pain, migraine and cardiac hypertrophy.

We have now found a group of novel compounds that are inhibitors of Raf kinases, in particular inhibitors of B-Raf kinase.

According to the invention there is provided compounds of formula (I):

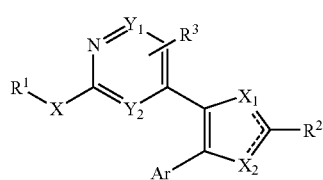

wherein;

X is O, $CH_2$, CO, S or NH, or the moiety X—$R^1$ is hydrogen;

$Y_1$ and $Y_2$ independently represent CH or N;

$R^1$ is hydrogen, $C_{1-6}$alkyl, $C_{3-7}$cycloalkyl, aryl, aryl$C_{1-6}$alkyl-, heterocyclyl, heterocyclyl$C_{1-6}$alkyl-, heteroaryl, or heteroaryl$C_{1-6}$alkyl-, any of which, except hydrogen, may be optionally substituted;

$R^2$ is hydrogen or an optionally substituted aryl or heteroaryl group;

Ar is a group of the formula a) or b):

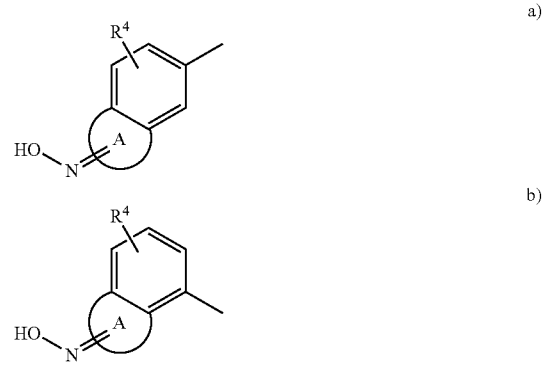

wherein A represents a fused 5- to 7-membered ring optionally containing up to two heteroatoms selected from O, S and $NR^5$, wherein $R^5$ is hydrogen or $C_{1-6}$alkyl, which ring is optionally substituted by up to 2 substituents selected from halogen, $C_{1-6}$alkyl, hydroxy, $C_{1-6}$alkoxy or keto;

$R^3$ and $R^4$ are independently selected from hydrogen, halogen, $C_{1-6}$alkyl, aryl, aryl$C_{1-6}$alkyl, $C_{1-6}$alkoxy, $C_{1-6}$alkoxy$C_{1-6}$alkyl, halo$C_{1-6}$alkyl, aryl$C_{1-6}$alkoxy, hydroxy, nitro, cyano, azido, amino, mono- and di-N—$C_{1-6}$alkylamino, acylamino, arylcarbonylamino, acyloxy, carboxy, carboxy salts, carboxy esters, carbamoyl, mono- and di-N—$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkyl sulphinyl or $C_{1-6}$alkylsulphonyl; and one of $X_1$ and $X_2$ is selected from O, S or $NR^{11}$ and the other is CH, wherein $R^{11}$ is hydrogen, $C_{1-6}$-alkyl, aryl or aryl$C_{1-6}$alkyl;

or pharmaceutically acceptable salts thereof.

As used herein, the double bond indicated by the dotted lines of formula (I), represents the possible regioisomeric ring forms of the compounds falling within the scope of this invention, the double bond being between the non-heteroatoms.

The hydroxyimino moiety can be positioned on any of carbon atoms of the non-aromatic ring in groups a) and b).

The hydroxyimino moiety can exist as either the E or Z isomer or as a mixture of both.

Alkyl and alkenyl groups referred to herein, individually or as part of larger groups e.g. alkoxy, may be straight or branched groups containing up to six carbon atoms and are optionally substituted by one or more groups selected from the group consisting of aryl, heteroaryl, heterocyclyl, $C_{1-6}$alkoxy, $C_{1-6}$alkylthio, aryl$C_{1-6}$alkoxy, aryl$C_{1-6}$alkylthio, amino, mono- or di-$C_{1-6}$alkylamino, cycloalkyl, cycloalkenyl, carboxy and esters thereof, amide, sulphonamido, ureido, guanidino, $C_{1-6}$-alkylguanidino, amidino, $C_{1-6}$alkylamidino, $C_{1-6}$acyloxy, azido, hydroxy, hydroxyimino and halogen.

Cycloalkyl and cycloalkenyl groups referred to herein include groups having from three to seven ring carbon atoms and are optionally substituted as described hereinabove for alkyl and alkenyl groups.

When used herein, the term "aryl" includes, unless otherwise defined, single and fused rings suitably containing from 4 to 7, preferably 5 or 6, ring atoms in each ring, which rings, may each be unsubstituted or substituted by, for example, up to three substituents.

Suitable aryl groups include phenyl and naphthyl, such as 1-naphthyl or 2-naphthyl.

Optional substituents for alkyl, alkenyl, cycloalkyl and cycloalkenyl groups include aryl, heteroaryl, heterocyclyl, $C_{1-6}$alkoxy, $C_{1-6}$-alkylthio, aryl$C_{1-6}$alkoxy, aryl$C_{1-6}$-alkylthio, amino, mono-or di-$C_{1-6}$alkylamino, aminosulphonyl, cycloalkyl, cycloalkenyl, carboxy and esters thereof, amide, ureido, quanidino, $C_{1-6}$alkylquanidino, amidino, $C_{1-6}$alkylamidino, $C_{1-6}$acyloxy, hydroxy, and halogen or any combination thereof. Preferably the substituents are mono-or di-$C_{1-6}$alkylamino, hetero$C_{3-6}$alkylamino or $C_{2-6}$acylamino.

Alternatively the optional substituent contains a water-solubilising group; suitable solubilising moieties will be apparent to those skilled in the art and include hydroxy and amine groups. Even more preferably the optional substituent includes amino, mono- or di-$C_{1-6}$alkylamino, amine containing heterocyclyl, or hydroxy or any combination thereof.

When used herein hetero$C_{1-6}$alkyl-means a $C_{1-6}$ carbon chain wherein the end carbon atom in the chain is substituted by a heteroatom selected from N, O, or S for example $C_{1-6}$alkylamino, $C_{1-6}$alkyloxy or $C_{1-6}$alkylthio.

$C_{1-6}$alkylhetero$C_{1-6}$-alkyl means a $C_{3-13}$alkyl chain wherein one of the carbon atoms has been replaced with a heteroatom selected from N, O, or S, for example $C_{1-6}$alkylamino$C_{1-6}$alkyl or $C_{1-6}$alkylaminodi$C_{1-6}$alkyl, $C_{1-6}$-alkyloxy$C_{1-6}$-alkyl-, $C_{1-6}$alkylthio$C_{1-6}$alkyl-, or $C_{1-6}$ alkylthiodi$C_{1-6}$alkyl.

When used herein the term "heterocyclyl" includes, unless otherwise defined, non-aromatic, single and fused, saturated or unsaturated, rings suitably containing up to four heteroatoms in each ring, each of which is selected from O, N and S, which rings, may be unsubstituted or substituted by, for example, up to three substituents. Each heterocyclic ring suitably has from 4 to 7, preferably 5 or 6, ring atoms. A fused heterocyclic ring system may include carbocyclic rings and need include only one heterocyclic ring. Examples of heterocyclyl groups include pyrrolidine, piperidine, piperazine, morpholine, thiomorpholine, imidazolidine and pyrazolidine.

When used herein, the term "heteroaryl" includes, unless otherwise defined, mono- and bicyclic heteroaromatic ring systems comprising up to four, preferably 1 or 2, heteroatoms each selected from O, N and S. Each ring may have from 4 to 7, preferably 5 or 6, ring atoms. A bicyclic heteroaromatic ring system may include a carbocyclic ring. Examples of heteroaryl groups include pyrrole, quinoline, isoquinoline, pyridine, pyrimidine, oxazole, thiazole, thiadiazole, triazole, imidazole and benzimidazole.

Aryl, heterocyclyl and heteroaryl groups may be optionally substituted by preferably up to three substituents. Suitable substituents include halogen, hydroxy, $C_{1-6}$-alkyl, aryl, aryl $C_{1-6}$alkyl, $C_{1-6}$alkoxy, $C_{1-6}$alkoxy $C_{1-6}$alkyl, halo $C_{1-6}$alkyl, aryl$C_{1-6}$alkoxy, hydroxy, nitro, cyano, azido, amino, mono- and di-N—$C_{1-6}$alkylamino, acylamino, arylcarbonylamino, acyloxy, amino$C_{1-6}$alkoxy, carboxy, carboxy salts, carboxy esters, carbamoyl, mono- and di-N—$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkylsulphinyl, $C_{1-6}$alkylsulphonyl, heterocyclyl, heteroaryl, heterocyclyl $C_{1-6}$alkyl, hydroxyimino-$C_{1-6}$alkyl and heteroaryl $C_{1-6}$alkyl, and combinations thereof.

Preferably the optional substituent contains a water-solubilising group; suitable solubilising moieties will be apparent to those skilled in the art and include hydroxy and amine groups. Even more preferably the optional substituent includes amino, mono- or di-$C_{1-6}$alkylamino, amine containing heterocyclyl, amino$C_{1-6}$alkoxy or hydroxy or any combination thereof.

When used herein halo means fluoro, chloro, bromo or iodo.

X is preferably NH or X—$R^1$ is preferably hydrogen.
When X is NH, $R^1$ is preferably hydrogen or $C_{1-6}$alkyl.
When $Y_1$ and $Y_2$ are CH, X—$R^1$ is preferably hydrogen.
When $Y_2$ is N, $R^1$ is preferably H or $C_{1-6}$alkyl.
Preferably $R^{11}$ is hydrogen.
Most preferably X—$R^1$ is hydrogen
Preferably $X_1$ or $X_2$ is O.
A is preferably a fused 5 membered ring optionally containing up to two heteroatoms selected from O, S and $NR^5$, wherein $R^5$ is hydrogen or $C_{1-6}$alkyl, which ring is optionally substituted by up to 2 substituents selected from halogen, $C_{1-6}$-alkyl, hydroxy, $C_{1-6}$-alkoxy or keto.

Even more preferably A is a fused 5 membered ring.
Preferably $R^2$ is hydrogen or an optionally substituted phenyl or pyrimidinyl.
Preferably $R^3$ is hydrogen or $C_{1-6}$alkyl.
Compounds wherein $X_1$ or $X_2$ is O are particularly preferred because a higher blood:brain ratio is achieved with these compounds.

Most preferably the compounds of the invention are of formula (II);

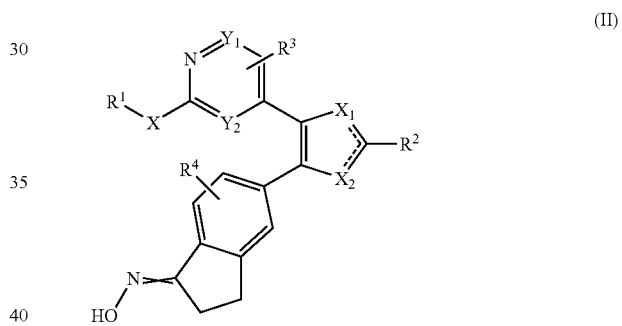

(II)

wherein $R^1$, X, $Y_1$, $Y_2$, $R^3$, $R^4$, $X_1$, $X_2$ and $R^2$ are as described for compounds of formula (I) or pharmaceutically acceptable salts thereof.

The compounds of formula (I) preferably have a molecular weight of less than 800.

Preferred substituents for the group Ar include halo, hydroxy, hydroxy $C_{1-6}$alkyl, hydroxyimino-$C_{1-6}$alkyl and $C_{1-6}$alkoxy.

It will be understood that the invention includes pharmaceutically acceptable derivatives of compounds of formula (I) and that these are included within the scope of the invention.

Particular compounds according to the invention include those mentioned in the examples and their pharmaceutically acceptable salts. As used herein "pharmaceutically acceptable derivatives" includes any pharmaceutically acceptable salt, ester or salt of such ester of a compound of formula (I) which, upon administration to the recipient, is capable of providing (directly or indirectly) a compound of formula (I) or an active metabolite or residue thereof.

It will be appreciated that for use in medicine the salts of the compounds of formula (I) should be pharmaceutically acceptable. Suitable pharmaceutically acceptable salts will be apparent to those skilled in the art and include those described in *J. Pharm. Sci.*, 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention.

The compounds of this invention may be in crystalline or non-crystalline form, and, if crystalline, may optionally be hydrated or solvated. This invention includes within its scope stoichiometric hydrates as well as compounds containing variable amounts of water.

The invention extends to all isomeric forms including stereoisomers and geometric isomers of the compounds of formula (I) including enantiomers and mixtures thereof e.g. racemates. The different isomeric forms may be separated or resolved one from the other by conventional methods, or any given isomer may be obtained by conventional synthetic methods or by stereospecific or asymmetric syntheses.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

Compounds of formula (I) are furan, pyrrole and thiophene derivatives which may be readily prepared, using procedures well-known to those skilled in the art, from starting materials which are either commercially available or can be prepared from such by analogy with well-known processes. For instance see, W. Friedrichsen (p351, furans), R. J. Sundberg (p119, pyrroles) and J. Nakayama (p607, thiophenes) in *Comprehensive Heterocyclic Chemistry II*, volume 2, series eds. A. R. Katritzky, C. W. Rees and E. F. V. Scriven, Typically, compounds of this invention may be prepared by a Paal-Knorr synthesis from a 1,4-dicarbonyl precursor, as outlined in Scheme 1 (where the groups —$XR^1$, $R^3$, and $R^4$ are hydrogen, and $Y_1$ and $Y_2$ are CH). For example, base (e.g. diethylamine) mediated condensation of an aryl-methyl ketone with pyridine4-carboxaldehyde results in the formation of a chalcone derivative (1, see S. E. deLaszlo et al *Bioorg. Med. Chem. Lett.*, 1999, 9, 641). Subsequent reaction of the chalcone (1) with a suitably protected (e.g. a methoxyimine, PG=MeON) derivative of indan-1-one-5-carboxaldehyde and catalytic sodium cyanide under Stetter conditions (H. Stetter and K. Kuhlmann, *Org. React.*, 1991, 40, 407) generates the aforementioned 1,4-dicarbonyl precursor (2). Cyclisation under the appropriate conditions then results in the formation of the desired furan (e.g. phosphorus pentoxide-methanesulphonic acid or concentrated sulphuric acid or HCl/acetone/dioxan), pyrrole (e.g. ammonium acetate, acetic acid) or thiophene (e.g. Lawessons reagent) ring systems (3). Thereafter, any substituents on the groups $R^2$, $X_1/X_2$ may be modified using conventional functional group interconversion procedures and the group PG may be converted into an hydroxyimino group as in (4). It will also be appreciated to one skilled in the art, that the aldehyde components could be utilised in reverse order generating the chalcone derivative (5) and subsequently the regioisomeric heterocycles (6).

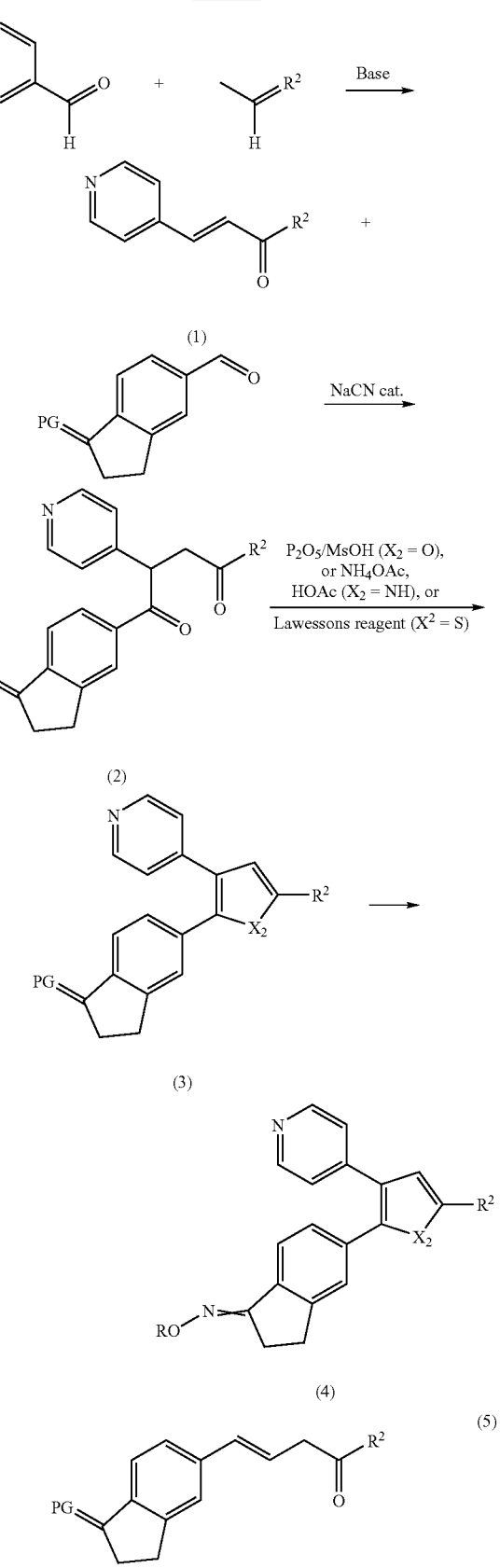

Scheme 1

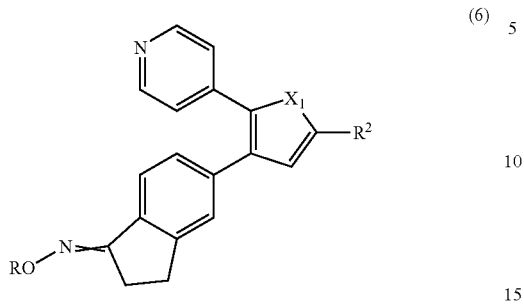

(6)

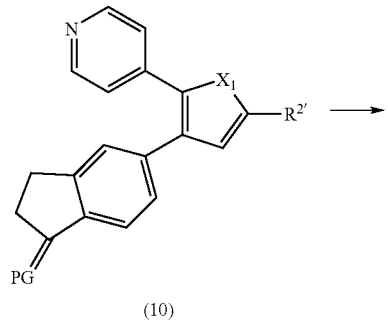

(10)

wherein $X_1$, $X_2$ and $R^2$ are as described for compounds of formula (I).

Compounds of this invention may also be prepared by sequential transition metal catalysed cross-coupling reactions on a 2,3-dihalo heterocycle, as shown in Scheme 2; this is particularly applicable for furan or thiophene derivatives, i.e. when one of $X_1$ or $X_2$ are O or S. For example, Suzuki coupling of pyridine4-boronic acid with a 2,3-dibromofuran derivative (7) preferentially results in the formation of the 2-(4-pyridyl)-3-bromo-furan (8). Subsequent Suzuki reaction with an indanone boronic acid derivative (9, wherein PG is O, N—OMe or another ketone protecting group) generates the derivative (10). Subsequently the group PG can also be converted into an hydroxyimino group as in (11). It will also be appreciated, to one skilled in the art, that the above cross-coupling reactions may be carried out in reverse order giving access to the regioisomeric heterocycles (12).

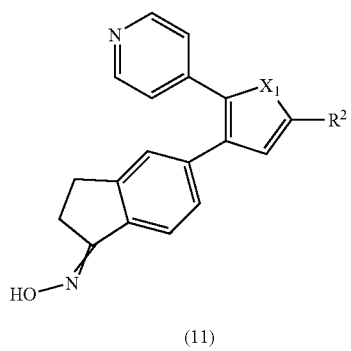

(11)

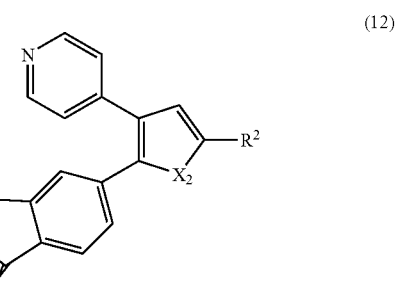

(12)

Scheme 2

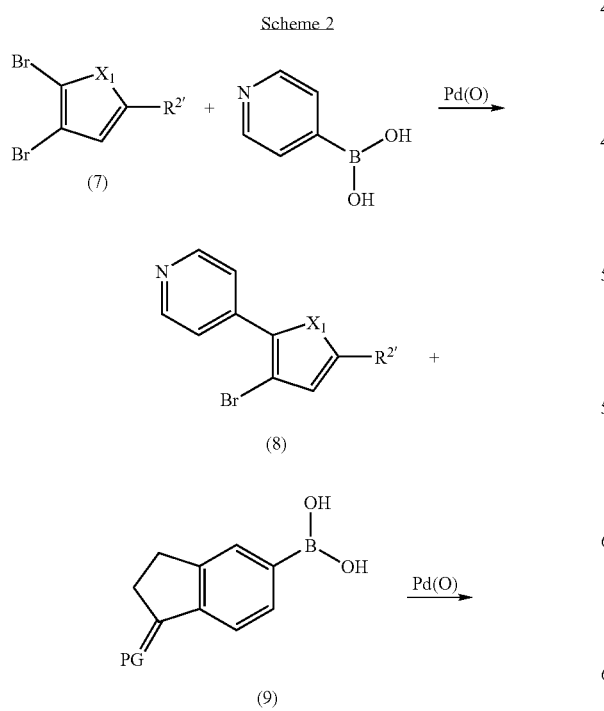

wherein $X_1X_2$ and $R^2$ are as described for compounds of formula (I).

During the synthesis of the compounds of formula (I) labile functional groups in the intermediate compounds, e.g. hydroxy, carboxy and amino groups, may be protected. A comprehensive discussion of the ways in which various labile functional groups may be protected and methods for cleaving the resulting protected derivatives is given in for example *Protective Groups in Organic Chemistry*, T. W. Greene and P. G. M. Wuts, (Wiley-Interscience, New York, 2nd edition, 1991).

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable salts thereof.

Pharmaceutically acceptable salts may be prepared conventionally by reaction with the appropriate acid or acid derivative.

As indicated above the compounds of formula (I) and their pharmaceutically acceptable derivatives are useful for the treatment and/or prophylaxis of disorders in which Raf kinases, in particular B-Raf kinase, are implicated.

According to a further aspect of the invention there is provided the use of a compound of formula (I) or a pharmaceutically acceptable salt thereof as an inhibitor of B-Raf kinase.

As indicated above the compounds of formula (I) and their pharmaceutically acceptable derivatives are useful in the treatment and/or prophylaxis of disorders associated with neuronal degeneration resulting from ischemic events, cancer, as well as chronic neurodegeneration, pain, migraine and cardiac hypertropy.

According to a further aspect of the invention there is provided a method of treatment or prophylaxis of a neurotraumatic disease, in a mammal in need thereof, which comprises administering to said mammal an effective amount of a compound of formula (I) or a pharmaceutically acceptable derivative thereof.

According to a further aspect of the invention there is provided the use of a compound of formula (I) or a pharmaceutically acceptable derivative thereof in the manufacture of a medicament for the prophylactic or therapeutic treatment of any disease state in a human, or other mammal, which is exacerbated or caused by a neurotraumatic event.

Neurotraumatic diseases/events as defined herein include both open or penetrating head trauma, such as caused by surgery, or a closed head trauma injury, such as caused by an injury to the head region. Also included within this definition is ischemic stroke, particularly to the brain area, transient ischemic attacks following coronary by-pass and cognitive decline following other transient ischemic conditions.

Ischemic stroke may be defined as a focal neurologic disorder that results from insufficient blood supply to a particular brain area, usually as a consequence of an embolus, thrombi, or local atheromatous closure of the blood vessel. Roles for stress stimuli (such as anoxia), redox injury, excessive neuronal excitatory stimulation and inflammatory cytokines in this area has been emerging and the present invention provides a means for the potential treatment of these injuries. Relatively little treatment, for an acute injury such as these has been available.

The compounds of the invention may also be used in the treatment or prophylaxis of cancers. It is suggested that the compounds are effective in tumors that have activating B-Raf mutations (V599E) as well as tumors that are activated by Ras mutation. Mutations may occur in the Ras family members such as Kras2 with mutation G13D. Furthermore compounds of the invention may be used in the treament or prophylaxis of colorectal cancer and melanoma.

According to a further aspect of the invention there is provided a method of treatment or prophylaxis of cancer, in a mammal in need thereof, which-comprises administering to said mammal an effective amount of a compound of formula (I) or a pharmaceutically acceptable derivative thereof.

According to a further aspect of the invention there is provided the use of a compound of formula (I) or a pharmaceutically acceptable derivative thereof in the manufacture of a medicament for the prophylactic or therapeutic treatment of cancers.

The compounds of formula (I) and pharmaceutically acceptable derivatives thereof, may be employed alone or in combination with other therapeutic agents for the treatment of the above-mentioned conditions. In particular, in anti-cancer therapy, combination with other chemotherapeutic, hormonal or antibody agents is envisaged as well as combination with surgical therapy and radiotherapy. Combination therapies according to the present invention thus comprise the administration of at least one compound of formula (I) or a pharmaceutically acceptable derivative thereof, and the use of at least one other cancer treatment method. Preferably, combination therapies according to the present invention comprise the administration of at least one compound of formula (I) or a pharmaceutically acceptable derivative thereof, and at least one other pharmaceutically active chemotherapeutic agent. These include existing and prospective chemotherapeutic agents. The compound(s) of formula (I) and the other pharmaceutically active chemotherapeutic agent(s) may be administered together in a unitary pharmaceutical composition or separately and, when administered separately this may occur simultaneously or sequentially in any order. Such sequential administration may be close in time or remote in time. The amounts of the compound(s) of formula (I) and the other pharmaceutically active chemotherapeutic agent(s) and the relative timings of administration will be selected in order to achieve the desired combined therapeutic effect.

Pharmaceutically active chemotherapeutic agents which can be useful in combination with a compound of formula (I) or a pharmaceutically acceptable derivative thereof, include but are not restricted to the following:

(1) cell cycle specific anti-neoplastic agents include, but are not limited to, diterpenoids such as paclitaxel and its analog docetaxel; tubulin poisons such as taxo/taxane or vinca alkaloids such as vinblastine, vincristine, vindesine, and vinorelbine; epipodophyllotoxins such as etoposide and teniposide; fluoropyrimidines such as 5-fluorouracil and fluorodeoxyuridine; antimetabolites such as allopurinol, fludarabine, methotrexate, cladrabine, cytarabine, mercaptopurine, gemcitabine, and thioguanine; and camptothecins such as 9-amino camptothecin, irinotecan, topotecan, and the various optical forms of 7-(4-methylpiperazino-methylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, dacarbazine and nitrosoureas; anti-tumour antibiotics such as doxorubicin, daunomycin, epirubicin, idarubicin, mitomycin-C, dactinomycin, bleomycin and mithramycin; and platinum coordination complexes such as cisplatin, carboplatin, and oxaliplatin; and (3) other chemotherapeutic agents including, but not limited to, anti-estrogens such as tamoxifen, toremifene, raloxifene, droloxifene and iodoxyfene; progestrogens such as megestrol acetate; aromatase inhibitors such as anastrozole, letrazole, vorazole, and exemestane; antiandrogens such as flutamide, nilutamide, bicalutamide, and cyproterone acetate; LHRH agonists and antagagonists such as goserelin acetate and luprolide, testosterone 5α-dihydroreductase inhibitors such as finasteride; metalloproteinase inhibitors such as marimastat; antiprogestrogens; mitoxantrone, 1-asparaginase, urokinase plasminogen activator receptor function inhibitors; inhibitors or c-kit and bcr/abl tyrosine kinases, (such as Gleevec), immunotherapy, immunoconjugates, cytokines (such as IL-2, IFN alpha and beta), tumor vaccines (including dendritic cell vaccines), thalidomide, COX-2 inhibitors, glucocorticoids (such as prednisone and decadron), radiation sensitizers, (such as temazolamide), growth factor function inhibitors such as inhibitors of the functions of hepatocyte growth factor; erb-B2, erb-B4, epidermal growth factor receptor (EGFR) and platelet derived growth factor receptors (PDGFR); inhibitors of angiogenesis such as inhibitors of the function of Ephrin receptors (such as, EphB4), vascular endothelial growth factor receptors (VEGFR) and the angiopoietin receptors (Tie1 and Tie2); and other kinase inhibitors such as inhibitors of CDK2 and CDK4.

Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

According to a further aspect of the invention there is provided a method of treatment or prophylaxis of chronic neurodegeneration, pain, migraine or cardiac hypertrophy, in a mammal in need thereof, which comprises administering to said mammal an effective amount of a compound of formula (I) or a pharmaceutically acceptable derivative thereof.

According to a further aspect of the invention there is provided the use of a compound of formula (I) or a pharmaceutically acceptable derivative thereof in the manufacture of a medicament for the prophylactic or therapeutic treatment of chronic neurodegeneration, pain, migraine or cardiac hypertrophy.

In order to use the compounds of formula (I) in therapy, they will normally be formulated into a pharmaceutical composition in accordance with standard pharmaceutical practice.

According to a further aspect of the invention there is provided a pharmaceutical composition comprising a compound of formula (I) or a pharmaceutically acceptable derivative thereof and a pharmaceutically acceptable carrier.

The compounds of formula (I) may conveniently be administered by any of the routes conventionally used for drug administration, for instance, parenterally, orally, topically or by inhalation. The compounds of formula (I) may be administered in conventional dosage forms prepared by combining it with standard pharmaceutical carriers according to conventional procedures. The compounds of formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable carrier is dictated by the amount of compound of formula (I) with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. When a liquid carrier is used, the preparation will be in the form of a syrup, emulsion, soft gelatin capsule, sterile injectable liquid such as an ampoule or nonaqueous liquid suspension.

The compounds of formula (I) are preferably administered parenterally, that is by intravenous, intramuscular, subcutaneous, sublingual, intranasal, intrarectal, intravaginal or intraperitoneal administration. The intravenous form of parenteral administration is generally preferred. The compounds may be administered as a bolus or continuous infusion e.g. over 6 hours to 3 days. Appropriate dosage forms for such administration may be prepared by conventional techniques.

The compounds of formula (I) may also be administered orally. Appropriate dosage forms for such administration may be prepared by conventional techniques.

The compounds of formula (I) may also be administered by inhalation, that is by intranasal and oral inhalation administration. Appropriate dosage forms for such administration, such as aerosol formulations, may be prepared by conventional techniques.

The compounds of formula (I) may also be administered topically, that is by non-systemic administration. This includes the application of the inhibitors externally to the epidermis or the buccal cavity and the instillation of such a compound into the ear, eye and nose, such that the compound does not significantly enter the blood stream.

For all methods of use disclosed herein the daily oral dosage regimen will preferably be from about 0.1 to about 80 mg/kg of total body weight, preferably from about 0.2 to 30 mg/kg, more preferably from about 0.5 to 15 mg/kg. The daily parenteral dosage regimen about 0.1 to about 80 mg/kg of total body weight, preferably from about 0.2 to about 30 mg/kg, and more preferably from about 0.5 to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of the inhibitors will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of the inhibitors given per day for a defined number of days, can be ascertained by those skilled in the art using conventional course of treatment determination tests. In the case of pharmaceutically acceptable salts the above figures are calculated as the parent compound of formula (I).

No toxicological effects are indicated/expected when a compound of formula (I) is administered in the above mentioned dosage range.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention and the following Descriptions illustrate the preparation of intermediates used in the preparation of these compounds.

Abbreviations used herein are as follows;
THF means tetrahydrofuran.
DMF means N,N-Dimethylformamide.

EXAMPLE 1

5-{5-[4(2-Dimethylaminoethoxy)phenyl]-3-pyridin-4yl-1H-pyrrol-2-yl}-indan-1-one oxime

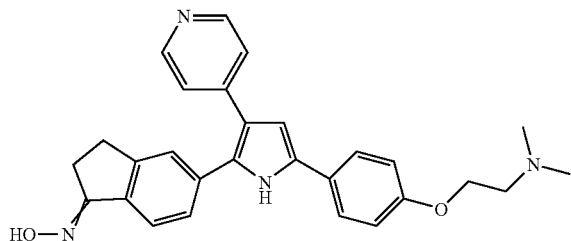

Step 1. 5-Bromoindan-1-one O-methyl-oxime

To a solution of 5-bromoindan-1-one (100 g, 0.47 mol) in ethanol (650 ml) under argon was added methoxylamine hydrochloride (198 g, 2.38 mol) and pyridine (125 ml). The mixture was heated under reflux for 2.5 hours, cooled to room temperature and poured into saturated aqueous sodium hydrogen carbonate solution. The mixture was extracted with ethyl acetate and the organic phase dried and concentrated in vacuo. The crude material was recrystallised from isopropanol to afford the title compound (110 g, 97%); $^1$H NMR (CDCl$_3$) 7.52 (1H, d, J 8.3 Hz), 7.43 (1H, d, J 1 Hz), 7.35 (1H, dd, J 8.3, 1 Hz), 3.97 (3H, s), 2.99 (2H, m), 2.85 (2H, m).

Step 2. 1-Methoxyiminoindan-5-carbaldehyde

A solution of the product of Step 1 (112 g, 0.46 mol) in tetrahydrofuran (1500 ml) at −60° C. under argon, was treated with n-butyllithium (325 ml of a 1.6M solution in hexanes, 0.52 mol) over 1 hour. After stirring at −60° C. for 1 hour a solution of dimethylformamide (39.7 ml) in tetrahydrofuran (50 ml) was added dropwise over 1 hour. The reaction was stirred at −60° C. for 1 hour before being allowed to warm to room temperature. After 1 hour the reaction was quenched with saturated aqueous sodium hydrogen carbonate solution and extracted into ethyl acetate. The organic phase was dried (MgSO$_4$), concentrated in vacuo and the residue chromatographed on silica gel eluting with dichloromethane to afford the title compound (57 g, 65%); $^1$H NMR (CDCl$_3$) 10.0 (1H, s), 7.83-7.73 (3H, m), 4.02 (3H, s), 3.10 (2H, m), 2.92 (2H, m).

Step 3. (E)-1-[4-(2-Dimethylaminoethoxy)phenyl]-3-pyridin-4-ylpropenone

A solution of dry pyridine (4.4 ml) under argon was treated with pyridine4-carboxaldehyde (2.14 g, 20 mmol) followed by 1-[4-(2-dimethylaminoethoxy)phenyl]ethanone (4.14 g, 20 mmol) (J. H. Short et al., J. Med. Chem., 1965, 8, 223) and diethylamine (2 ml, 20 mmol). The solution was heated under reflux for 18 hours, cooled to room temperature and poured into ice water (100 ml) containing concentrated hydrochloric acid (10 ml). The resulting solution was adjusted to pH 9 by addition of sodium hydroxide solution. The mixture was extracted with ethyl acetate and the organic phase washed with water and saturated brine, dried (MgSO$_4$) and concentrated in vacuo. The residue was triturated with diethyl ether to afford the title compound (3.7 g, 63%); MS(ES+) m/e 297 [M+H]+.

Step 4. 4-[4(2-Dimethylaminoethoxy)phenyl]-1-(1-methoxyiminoindan-5-yl)-2-pyridin-4-ylbutane-1,4-dione A solution of sodium cyanide (0.033 g, 0.67 mmol) in dimethylformamide (5 ml) at room temperature was treated with a solution of the product of Step 2 (1.4 g, 7.4 mmol) in dimethylformamide (4 ml) over 15 minutes. After stirring for 15 minutes a solution of the product of Step 3 (2.0 g, 6.7 mmol) in dimethylformamide (10 ml) was added dropwise. The mixture was stirred at room temperature for 18 hours, diluted with water and the pH of the solution adjusted to 9 with saturated sodium hydrogen carbonate solution. The mixture was extracted into chloroform and the organic phase washed with water and brine, dried (MgSO$_4$) and concentrated in vacuo. The residue was chromatographed on silica gel eluting with 0.880 ammonia/ethanol/chloroform solution (1:9:90) to afford the title compound; MS(ES+) m/e 486 [M+H]+.

Step 5. 5-{5-[4-(2-Dimethylaminoethoxy)phenyl]-3-pyridin-4yl-1H-pyrrol-2-yl}indan-1-one O-methyl-oxime A solution of the product of Step 4 (0.45 g, 1 mmol) and ammonium acetate (0.77 g, 10 mmol) in glacial acetic acid (15 ml) was heated under reflux for 3 hours. After cooling to room temperature the reaction mixture was concentrated in vacuo and saturated sodium hydrogen carbonate solution was added. The mixture was extracted with chloroform and the organic phase washed with water and brine, dried and concentrated in vacuo to afford the title compound (0.47 g, 100%); MS(ES+) m/e 467 [M+H]+.

Step 6. 5-{5-[4-(2-Dimethylaminoethoxy)phenyl]-3-pyridin-4-yl-1H-pyrrol-2-yl}indan-1-one A solution of the product of Step 5 (0.47 g, 1 mmol) in 1,4-dioxane (10 ml), 5M hydrochloric acid (5 ml) and acetone (10 ml) was heated under reflux for 2 hours. After cooling to room temperature the reaction mixture was concentrated in vacuo and the residue was azeotroped twice with acetone/ethanol to afford the dihydrochloride salt of the title compound which was used directly in the next step; MS(ES+) m/e 438 [M+H]+.

Step 7. 5-{5-[4-(2-Dimethylaminoethoxy)phenyl]-3-pyridin-4-yl-1H-pyrrol-2-yl}indan-1-one oxime A solution of the product of Step 6 in ethanol (20 ml) containing aqueous hydroxylamine (5 ml, 50% in water) was heated under reflux for 1 hour. After cooling to room temperature, the mixture was concentrated and the residue partitioned between chloroform and saturated sodium hydrogen carbonate solution. The organic phase was washed with water and saturated brine, dried (MgSO₄) and concentrated in vacuo. The residue was chromatographed on silica gel eluting with 0.880 ammonia/ethanol/chloroform solution (1:9:90) to afford the title compound (0.085 g); MS(ES+) m/e 453 [M+H]+.

EXAMPLE 2

5-{5-[4(2-Dimethylaminoethoxy)phenyl]-2-pyridin-4-yl-1H-pyrrol-3-yl}-indan-1-one oxime

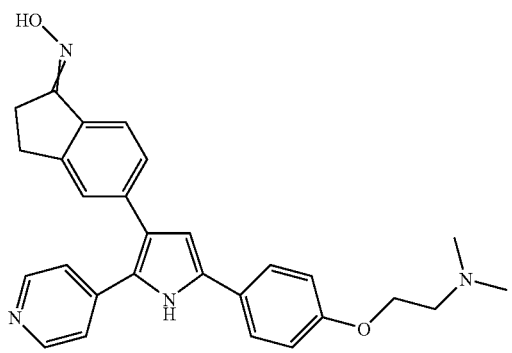

Step 1. 5-{(E)-3-[4-(2-Dimethylamino-ethoxy)-phenyl]-3-oxo-propenyl}-indan-1-one O-methyl oxime A solution of the product of Example 1 Step 2 (1.06 g, 5.6 mmol), sodium methoxide (0.750 g, 13.9 mmol) and 1-[4-(2-dimethylaminoethoxy) phenyl]ethanone hydrochloride (1.36 g, 5.6 mmol) (J. H. Short et al., *J. Med. Chem.* 1965, 8, 223) in methanol (30 ml) and water (1 ml) was heated under reflux for 5 hours. After cooling to room temperature the solid was collected, washed with cold methanol and diethyl ether and dried to give the title compound (1.74 g, 83%); MS(ES+) m/e 378 [M+H]+.

Step 2. 4-[4(2-Dimethylaminoethoxy)phenyl]-2-(1-methoxyiminoindan-5-yl)-1-pyridin-4-ylbutane-1,4-dione The title compound was prepared from the product of Step 1 and pyridine-4-carboxaldehyde using the method described in Example 1 Step 4; MS(ES+) m/e 486 [M+H]+.

Step 3. 5-{5-[4-(2-Dimethylaminoethoxy)phenyl]-2-pyridin-4-yl-1H-pyrrol-3-yl}indan-1-one oxime The title compound was prepared from the product of Step 2 using the methods described in Example 1 Steps 5-7; MS(ES+) m/e. 453 [M+H]+.

EXAMPLE 3

5-{5-[4-(2-Dimethylaminoethoxy)phenyl]-3-pyridin-4ylfuran-2-yl}indan-1-one oxime

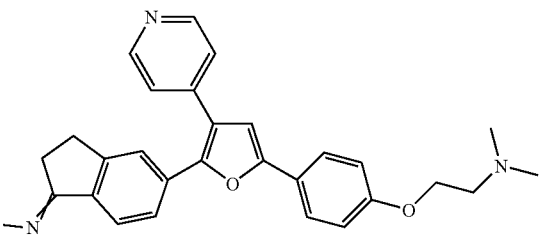

Step 1. 5-{5-[4-(2-Dimethylaminoethoxy)phenyl]-3-pyridin-4-ylfuran-2-yl}indan-1-one O-methyl-oxime The product of Example 1 Step 4 (0.30 mg, 0.62 mmol) was added to a stirred suspension of phosphorus pentoxide (1 g) in dry methane sulphonic acid (5 ml). After stirring at room temperature for 2 hours the reaction mixture was cautiously poured into a stirred solution of saturated aqueous sodium hydrogen carbonate. The mixture was extracted with ethyl acetate and the organic phase washed with water and saturated brine, dried (MgSO₄) and concentrated in vacuo to afford the title compound (0.28 g, 96%); MS(ES+) m/e 468 [M+H]+.

Step 2. 5-{5-[4-(2-Dimethylaminoethoxy)phenyl]-3-pyridin-4ylfuran-2-yl}indan-1-one oxime The title compound (76 mg, 45%) was prepared from the product of Step 1 using the methods described in Example 1 Steps 6 and 7; MS(ES+) m/e 454 [M+H]+.

EXAMPLE 4

5-{5-[4-(2-Dimethylaminoethoxy)phenyl]-2-pyridin-4yl-furan-3-yl}indan-1-one oxime

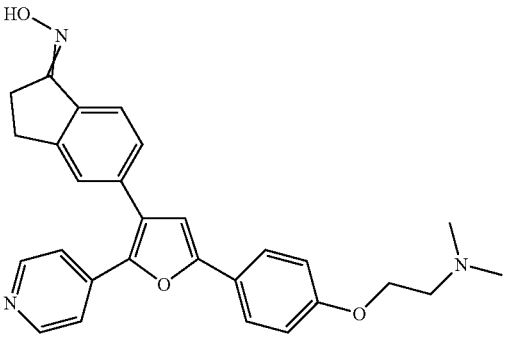

The title compound was prepared from the product of Example 2 Step 2 (300 mg, 0.62 mmol) using the procedures described in Example 3 Steps 1 and 2; MS(ES+) m/e 454 [M+H]+.

EXAMPLE 5

5-{5-[2-(2-Dimethylaminoethoxy)pyrimidin-5-yl]-2-pyridin-4-ylfuran-3-yl}indan-1-one oxime

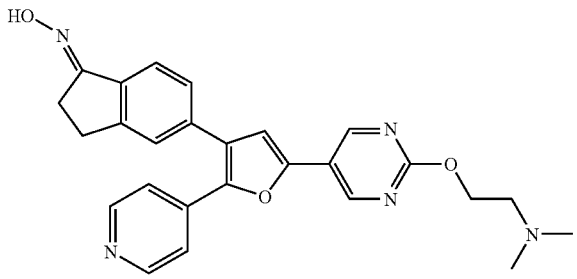

Step 1. 5-Bromo-2-methylsufanylpyrimidine

A solution of 2-methylsulfanylpyrimidine (Dawood et al., *J. Org. Chem.*, 1999, 64, 21, 7935) (19.8 g, 157 mmol) in carbon tetrachloride (300 ml) and 1,2-dichloroethane (150 ml) was treated with bromine (8.1 ml, 157 mmol) and heated under reflux for 6 days. After cooling to room temperature, 20% aqueous sodium sulphite solution (250 ml) was added and the mixture stirred for 1 hour. The layers were separated and the aqueous phase extracted into dichloromethane. The combined organic extracts were dried (MgSO$_4$), concentrated in vacuo and the residue chromatographed on silica gel eluting with a mixture of ethyl acetate/hexane (5:95) to afford the title compound (13.0 g, 40%); $^1$H NMR (CDCl$_3$) 8.56 (2H, s), 2.55 (3H, s).

Step 2. 5-Bromo-2-methanesulfonylpyrimidine

A suspension of the product of Step 1 (1.0 g, 4.9 mmol) and oxone (6.0 g, 9.8 mmol) in methanol (40 ml) and water (40 ml) was stirred at room temperature for 4 hours. The reaction mixture was poured into dichloromethane, the layers separated and the organic layer dried (MgSO$_4$) and concentrated in vacuo to afford the title compound (1.0 g, 86%); $^1$H NM (CDCl$_3$) 8.99 (2H, s), 3.36 (3H, s).

Step 3. [2-(5-Bromopyrimidin-2-yloxy)ethyl]dimethylamine

A solution of N,N-dimethylethanolamine (0.23 ml, 2.3 mmol) in dry dimethylformamide (5 ml) was treated with sodium hydride (60% suspension in mineral oil, 0.092 g, 2.3 mmol) and heated at 50° C. for 30 minutes. The product from Step 2 (0.50 g, 2.1 mmol) was added and the reaction heated at 50° C. overnight. After cooling to room temperature the reaction mixture was applied to a SCX column and washed with methanol then a mixture of 0.880 ammonia/methanol (1:9). The basic fractions were combined and chromatographed on silica gel eluting with 0.880 ammonia/methanol/dichloromethane solution (0.1:1.9:98 and 0.5:4.5:95) to afford the title compound (0.25 g, 48%); $^1$H NMR (CDCl$_3$) 8.52 (2H, s), 4.45 (2H, t, J 8 Hz), 2.74 (2H, t, J 8 Hz), 2.33 (6H, s).

Step 4. Dimethyl-[2-(5-trimethylstannanylpyrimidin-2-yloxy)ethyl]amine

A solution of the product from Step 3 (0.25 g, 10 mmol) in dry toluene (5 ml) was treated with bis(triphenylphosphine)palladium (II) chloride (0.071 g, 0.1 mmol) and hexamethylditin (0.66 g, 2.0 mmol) and heated at 100° C. for 1 hour. After cooling to room temperature the reaction mixture was applied to a SCX column and washed with methanol then a mixture of 0.880 ammonia/methanol (1:9). The basic fractions were combined and chromatographed on silica gel eluting with 0.880 ammonia/methanol/dichloromethane solution (0.1:1.9:98 and 0.5:4.5:95) to afford the title compound (0.20 g, 61%); $^1$H NMR (CDCl$_3$) 8.46 (2H, s), 7.26 (2H, s), 4.46 (2H, t, J 8 Hz), 2.76 (2H, t, J 8 Hz), 2.34 (6H, s), 0.35 (9H, s).

Step 5. 4(3-Bromofuran-2-yl)pyridine

A solution of tributylstannylpyridine (8.0 g, 21.7 mmol) and 2,3-dibromofuran (5.9 g, 26.1 mmol) in dry toluene (200 ml) was treated with bis(triphenylphosphine)palladium (II) chloride (1.5 g, 2.2 mmol) and heated at 100° C. overnight. After cooling to room temperature, the reaction mixture was diluted with ethyl acetate, washed with water, dried (MgSO$_4$) and evaporated in vacuo. The residue was chromatographed on silica gel eluting with ethyl acetate to afford the title compound (1.2 g, 25%); $^1$H NMR (CDCl$_3$) 8.66 (2H, d, J 11 Hz), 7.84 (2H, d, J 11 Hz), 7.50 (1H, d, J 3 Hz), 6.60 (1H, d, J 3 Hz).

Step 6. 1-Methoxyiminoindan-5-boronic acid

A solution of the product of Example 1 Step 1 (48.0 g, 0.2 mol) in tetrahydrofuran (1 L) at −78° C. under argon atmosphere was treated dropwise with n-butyl lithium (138 ml, 1.6M in hexanes, 0.22 mol). After stirring at −78° C. for 30 minutes trimethyl borate (49 ml, 0.44 mol) was added and the solution warmed to room temperature and stirred for 16 hours. The mixture was concentrated in vacuo, acidified to pH1 with 5N hydrochloric acid and stirred at room temperature for 1 hour. The mixture was then basified with 40% sodium hydroxide and the solution washed three times with diethyl ether. The aqueous phase was re-acidified to pH 1 and the mixture was extracted five times with ethyl acetate. The organic extracts were combined washed with brine, dried and evaporated in vacuo. The residue was triturated with hexane, filtered, washed with hexane and then a small amount of ether to afford the title compound (23.6 g, 58%); MS(AP−) m/e 204 [M−H]−.

Step 7. 5-(2-Pyridin-4-ylfuran-3-yl)indan-1-one O-methyl oxime

A solution of the product of Step 5 (1.2 g, 5.4 mmol) and the product of Step 6 (2.2 g, 6.4 mmol) in 1,2-dimethoxyethane (40 ml) and water (20 ml) was treated with potassium carbonate (6.0 g, 43.2 mmol), palladium acetate (0.06 g, 0.27 mmol) and triphenylphosphine (0.14 g, 0.54 mmol) and heated under reflux for 1.5 hours. After cooling to room temperature, the reaction mixture was poured into water, extracted into ethyl acetate, dried (MgSO$_4$) and concentrated in vacuo. The residue was chromatographed on silica gel eluting with ethyl acetate to afford the title compound (1.0 g, 61%); MS(ES+) m/e 305 [M+H]$^+$.

Step 8. 5-(2-Pyridin-4ylfuran-3-yl)indan-1-one

The title compound (1.7 g, 94%) was prepared from the product of Step 7 (2.0 g, 6.6 mmol) using the method of Example 1 Step 6; MS(ES+) m/e 276 [M+H]+.

Step 9. 5-(5-Bromo-2-pyridin-4-ylfuran-3-yl)indan-1-one

A solution of the product of Step 8 (1.0 g, 3.6 mmol) in dry dimethylformamide (10 ml) was treated with freshly recrystallised N-bromosuccinimide (1.42 g, 8.0 mmol) and heated at 50° C. for 1 hour. After cooling to room temperature, the reaction mixture was poured into saturated aqueous sodium hydrogen carbonate solution, extracted into dichloromethane, washed twice with brine, dried ($MgSO_4$) and concentrated in vacuo. The residue was chromatographed on silica gel eluting with ethyl acetate to afford the title compound (0.2 g, 16%); $^1$H NMR ($CDCl_3$) 8.52 (2H, d, J 8 Hz), 7.80 (1H, d, J 11 Hz), 7.49 (1H, s), 7.38 (1H, d, J 8 Hz), 7.32 (2H, d, J 8 Hz), 6.54 (1H, s), 3.17 (2H, t, J 5 Hz), 2.75 (2H, t, 5 Hz).

Step 10.5-{5-[2-(2-Dimethylaminoethoxy)pyrimidin-5-yl]-2-pyridin-4-ylfuran-3-yl}indan-1-one A solution of the product of Step 9 (0.1 g, 0.282 mmol) in dry toluene (2 ml) was treated with bis(triphenylphosphine)palladium(II) choride (0.02 g, 0.0282 mmol) and the product of Step 4 and the reaction heated at 100° C. for 18 hours. After cooling to room temperature the reaction mixture was applied to a SCX column and washed with methanol then a mixture of 0.880 ammonia/methanol (1:9). The basic fractions were combined and chromatographed on silica gel eluting with 0.880 ammonia/methanol/dichloromethane solution (0.7:6.3:93) to afford the title compound (0.060 g, 0.136 mmol; MS(ES+) m/e 441 [M+H]+.

Step 11.5-{5-[2-(2-Dimethylaminoethoxy)pyrimidin-5-yl]-2-pyridin-4-ylfuran-3-yl}indan-1-one oxime The title compound (0.25 g, 39%) was prepared from the product of Step 10 using the method of Example 1 Step 7; MS(ES+) m/e 456 [M+H]+.

EXAMPLE 6

5-{5-[2-(2-Morpholin-4-ylethoxy)pyrimidin-5-yl]-2-pyridin-4-ylfuran-3-yl}indan-1-one oxime

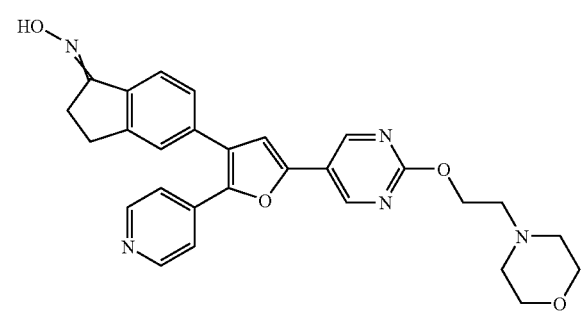

Step 1. 4-[2-(5-Bromopyrimidin-2-yloxy)ethyl]morpholine

The title compound (0.26 g, 43%) was prepared from the product of Example 5 Step 2 and 4-(2-hydroxyethylmorpholine) using the method of Example 5 Step 3; $^1$H NMR ($CDCl_3$) 8.52 (2H, s), 4.49 (2H, t, J 8 Hz), 3.71 (4H, t, J 5 Hz), 2.81 (2H, t, J 8 Hz), 2.57 (4H, t, J 5 Hz).

Step 2. 4-[2-(5-Trimethylstannanylpyrimidin-2-yloxy)ethyl]morpholine

The title compound (0.2 g, 60%) was prepared from the product of Step 1 using the method of Example 5 Step 4; $^1$H NMR ($CDCl_3$) 8.51 (2H, s), 4.50 (2H, t, J 7 Hz), 3.71 (4H, t, J 6 Hz), 2.82 (2H, t, J 7 Hz), 2.59 (4H, t, J 6 Hz), 0.35 (9H, s).

Step 3. 5-{5-[2-(2-Morpholin-4-ylethoxy)pyrimidin-5-yl]-2-pyridin-4ylfuran-3-yl}indan-1-one The title compound (0.11 g, 48%) was prepared from the product of Step 2 and the product from Example 5 Step 9 using the method of Example 5 Step 10; MS(ES+) m/e 483 [M+H]+.

Step 4. 5-{5-[2-(2-Morpholin-4-ylethoxy)pyrimidin-5-yl]-2-pyridin-ylfuran-3-yl}indan-1-one oxime The title compound (0.06 g, 52%) was prepared from the product of Step 3 using the method of Example 1 Step 7; MS(ES+) m/e 498 [M+H]+.

EXAMPLE 7

5-{5-[2-(4-Methylpiperazin-1-yl)pyrimidin-5-yl]-2-pyridin-4-ylfuran-3-yl}indan-1-one oxime

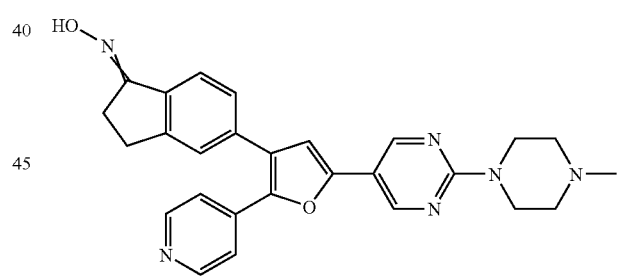

Step 1. 1-(2-Methylsulfanylpyrimidin-5-yl)ethanone

The product of Example 5 Step 1 (13.0 g, 63.4 mmol) in dry toluene (200ml) was treated with 1-ethoxyvinyltributyl tin (25.2 g, 69.8 mmol) and bis(triphenylphosphine)palladium(II) chloride (2.2 g, 3.2 mmol) and heated at 100° C. for 18 hours. After cooling to room temperature, the solvent was removed in vacuo and the residue dissolved in tetrahydrofuran, treated with 0.5N hydrochloric acid (40 ml) and stirred at room temperature for 1 hour. The reaction mixture was diluted with water, extracted into dichloromethane, dried ($MgSO_4$) and evaporated in vacuo. The residue was chromatographed on silica gel eluting with a mixture of ethyl acetate/hexane (1:4 then 1:1) to afford the title compound (3.3 g, 31%); $^1$H NMR ($CDCl_3$) 9.00 (2H, s), 2.62 (3H, s) 2.58(3H, s).

Step 2. 5-[(E)-3-(2-Methylsulfanylpyrimidin-5-yl)-3-oxopropenyl]indan-1-one O-methyloxime The title compound (2.6 g, 28%) was prepared from the product of Step 1 and the product of Example 1 Step 2 using the method of Example 2 Step 1; MS(ES+) m/e 340 [M+H]+.

Step 3. 2-(1-Methoxyiminoindan-5-yl)-4-(2-methylsulfanylpyrimidin-5-yl)-1-pyridin-4-ylbutane-1,4-dione The title compound (2.9 g, 74%) was prepared from the product of Step 2 and 4-pyridinecarboxaldehyde using the method of Example 1 Step 4; MS(ES+) m/e 447 [M+H]+.

Step 4. 5-[5-(2-Methylsulfanylpyrimidin-5-yl)-2-pyridin-4-ylfuran-3-yl]indan-1-one O-methyloxime The title compound (0.36 g, 65%) was prepared from the product of Step 3 using the method of Example 3 Step 1; MS(ES+) m/e 429 [M+H]+.

Step 5. 5-[5-(2-Methylsulfanylpyrimidin-5-yl)-2-pyridin-4-ylfuran-3-yl]indan-1-one The title compound (1.6 g, 62%) was prepared from the product of Step 4 using the method of Example 1 Step 6; MS(ES+) m/e 400 [M+H]+.

Step 6. 5-[5-(2-Methanesulfonylpyrimidin-5-yl)-2-pyridin-4ylfuran-3-yl]indan-1-one A solution of the product of Step 5 (1.4 g, 3.5 mmol) in water (70 ml) and 2N hydrochloric acid (5.25 ml, 10.5 mmol) was treated with sodium tungstate dihydrate (100 mg, 0.36 mmol) and 30% hydrogen peroxide solution (2.4 g, 21 mmol) and stirred at room temperature for 18 hours. The reaction mixture was poured into aqueous sodium thiosulphate solution, basified with saturated aqueous sodium hydrogen carbonate solution, extracted into dichloromethane, dried (MgSO4) and evaporated in vacuo to afford the title compound (0.70 g, 46%); MS(ES+) m/e 432 [M+H]+.

Step 7. 5-{5-[2-(4-Methylpiperazin-1-yl)pyrimidin-5-yl]-2-pyridin-4-ylfuran-3-yl}indan-1-one A solution of the product from Step 6 (0.15 g, 0.35 mmol) in dry dimethylformamide (2 ml) was treated with N-methylpiperazine (0.077 ml, 0.70 mmol) and heated at 90° C. for 2 hours. After cooling to room temperature the reaction mixture was applied to a SCX column and washed with methanol then a mixture of 0.880 ammonia/methanol (1:9). The basic fractions were combined and chromatographed on silica gel eluting with 0.880 ammonia/methanol/dichloromethane solution (0.5:4.5:95) to afford the title compound (0.09 g, 57%); MS(ES+) m/e 452 [M+H]+.

Step 8. 5-{5-[2-(4-Methylpiperazin-1-yl)pyrimidin-5-yl]-2-pyridin-4-ylfuran-3-yl}indan-1-one oxime The title compound (0.07 g, 75%) was prepared from the product of Step 7 using the method of Example 1 Step 7; MS(ES+) m/e 467 [M+H]+.

EXAMPLE 8

5-[5-(2-Piperazin-1-ylpyrimidin-5-yl)-2-pyridin-4-ylfuran-3-yl]indan-1-one oxime

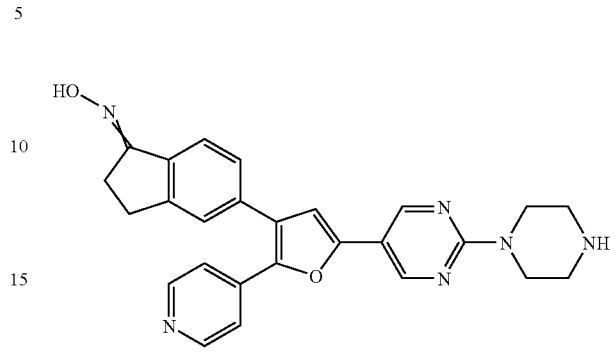

Step 1. 5-[5-(2-Piperazin-1-ylpyrimidin-5-yl)-2-pyridin-4-ylfuran-3-yl]indan-1-one The title compound (0.10 g, 65%) was prepared from the product of Example 7 Step 6 and piperazine using the method of Example 7 Step 7; MS(ES+) m/e 438 [M+H]+.

Step 2. 5-[5-(2-Piperazin-1-ylpyrimidin-5-yl)-2-pyridin-4-ylfuran-3-yl]indan-1-one oxime The title compound (0.034 g, 33%) was prepared from the product of Step 1 using the method of Example 1 Step 7; MS(ES+) m/e 453 [M+H]+.

EXAMPLE 9

5-{5-[2-(2-Dimethylaminoethylamino)pyrimidin-5-yl]-2-pyridin-4-yl-furan-3-yl}indan-1-one oxime

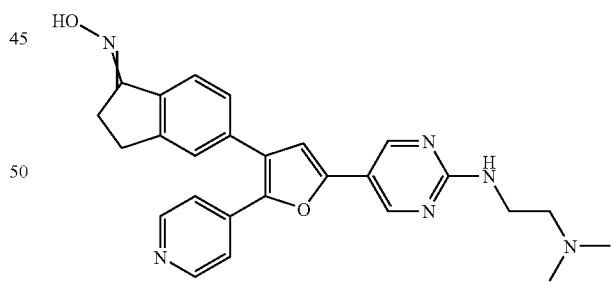

Step 1. 5-{5-[2-(2-Dimethylaminoethylamino)pyrimidin-5-yl]-2-pyridin-4-ylfuran-3-yl}-indan-1-one The title compound (0.03 g, 20%) was prepared from the product of Example 7 Step 6 and N,N-dimethylethylenediamine using the method of Example 7 Step 7; $^1$H NMR (CDCl$_3$) 8.68 (2H, s), 8.52 (2H, d, J 8 Hz), 7.82 (1H, d, J 10 Hz), 7.57 (H, s), 7.46 (1H, d, J 10 Hz), 7.39 (2H, J 8 Hz), 6.67 (1H, s), 5.90 (1H, m), 3.53 (2H, m), 3.18 (2H, t, J 5 Hz), 2.77 (2H, t, J 8 Hz,), 2.56 (2H, t, J 5 Hz) 2.29 (6H, s).

Step 2. 5-{5-[2-(2-Dimethylaminoethylamino)pyrimidin-5-yl]-2-pyridin-4-yl-furan-3-yl}indan-1-one oxime The title compound (0.015 g, 47%) was prepared from the product of Step 1 using the method of Example 1 Step 7; MS(ES+) m/e 455 [M+H]$^+$.

EXAMPLE 10

5-{5-[4-(2-Dimethylaminoethoxy)phenyl]-3-(2-methylpyridin-4-yl-furan-2-yl}indan-1-one oxime

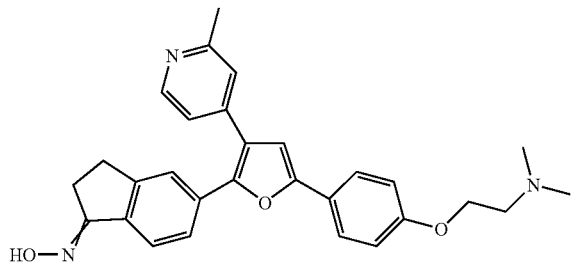

The title compound was prepared from 4-formyl-2-methylpyridine and 1-[4-(2-dimethylaminoethoxy)phenyl]ethanone using the methods described in Example 1 Steps 3 and 4 followed by Example 3 Steps 1-3; MS(ES+) m/e 468 [M+H]$^+$.

EXAMPLE 11

5-{2-(2-Aminopyrimidin-4-yl)-5-[4(2-dimethylaminoethoxy)phenyl]furan-3-yl}indan-1-one oxime

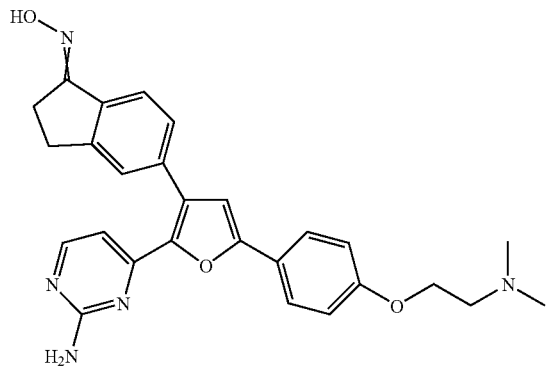

Step 1. 4-[4-(2-Dimethylaminoethoxy)phenyl]-2-(1-methoxyiminoindan-5-yl)-1-pyridin-4-ylbutane-1,4-dione The title compound (1.17 g, 70%) was prepared from the product of Example 2 Step 1 and 2-methylsulfanylpyrimidine-4-carbaldehyde (U.S. Pat. No. 6,046,208) using the method of Example 1 Step 4; MS(ES+) m/e 533 [M+H]+.

Step 2. 5-[5-[4-(2-Dimethylamino-ethoxy)-phenyl]-2-(2-methylsulfanylpyrimidin-4-yl)furan-3-yl]indan-1-one The title compound (100 mg, 87%) was prepared from the product of Step 1 using the methods described in Example 3 Steps 1 and 2; MS(ES+) m/e 487 [M+H]+.

Step 3. 5-[5-[4-(2-Dimethylaminoethoxy)phenyl-5-2-(2-methanesulfonylpyrimidin-4-yl)-furan-3-yl]-indan-1-one The title compound (0.051 g, 96%) was prepared from the product of Step 2 using the method of Example 7 Step 6; MS(ES+) m/e 518 [M+H]$^+$.

Step 4. 5-{2-(2-Aminopyrimidin-4-yl)-5-[4-(2-dimethylaminoethoxy)phenyl]furan-3-yl}-indan-1-one A solution of the product of Step 3 (0.052 g, 0.1 mmol) in tetrahydrofuran (3 ml) was treated with 0.880 ammonia solution (3 ml). The reaction mixture was then heated at 100° C. in an autoclave for 18 hours, cooled to 0° C. and extracted into chloroform. The organic extracts were then dried (Na$_2$SO$_4$) and concentrated in vacuo. The residue was chromatographed on silica gel eluting with a mixture of 0.880 ammonia/methanol/chloroform solution (0.6:5.4:94) to afford the title compound (0.017 g, 0.037 mmol); MS(ES+) m/e 455 [M+H]$^+$.

Step 5. 5-{2-(2-Aminopyrimidin-4-yl)-5-[4-(2-dimethylaminoethoxy)phenyl]furan-3-yl}indan-1-one oxime The title compound was prepared from the product of Step 4 using the method of Example 1 Step 7; MS(ES+) m/e 470 [M+H]$^+$.

EXAMPLE 12

5-{2-Pyridin-4-yl-5-[4-(2-pyrrolidin-1-ylethoxy)phenyl]furan-3-yl}indan-1-one oxime

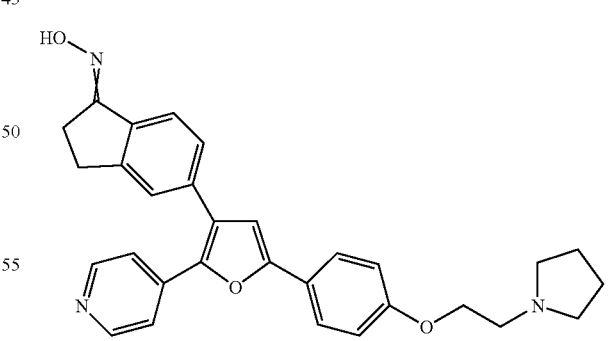

Step 1. 5-[(E)3-(4Methoxyphenyl)-3-oxopropenyl]indan-1-one O-methyloxime

The title compound (7.75 g, 91%) was prepared from the product of Example 1 Step 2 and 1-(4-methoxy-phenyl)ethanone using the method of Example 2 Step 1; MS(ES+) m/e 322 [M+H]+.

Step 2. 2-(1-Methoxyiminoindan-5-yl)-4-(4methoxyphenyl)-1-pyridin-4-ylbutane-1,4 dione The title compound (8.82 g, 86%) was prepared from the product of Step 1 and pyridine-4-carboxaldehyde fusing the method of Example 1 Step 4; MS(ES+) m/e 429 [M+H]+.

Step 3. 5-[5-(4-Methoxyphenyl)-2-pyridin-4-ylfuran-3-yl]indan-1-one O-methyloxime The title compound (8.4 g, 98%) was prepared from the product of Step 2 using the method of Example 3 Step 1; MS(ES+) m/e 411 [M+H]+.

Step 4. 5-[5-(4Methoxyphenyl)-2-pyridin-4-ylfuran-3-yl]indan-1-one

The title compound (3.0 g, 38%) was prepared from the product of Step 3 using the method described in Example 3 Step 2; MS(ES+) m/e 382 [M+H]+.

Step 5. 5-[5-(4-Hydroxyphenyl)-2-pyridin-4-ylfuran-3-yl]indan-1-one

A solution of the product of Step 4 (100 mg, 0.26 mmol) in dichloromethane (2 ml) was treated at 0° C. with boron tribromide (1.3 ml of a 1M solution in dichloromethane, 1.3 mmol) and stirred at room temperature for 1 hour. The reaction mixture was poured into saturated sodium bicarbonate solution extracted into dichoromethane, dried ($Na_2SO_4$) and concentrated in vacuo. The residue was dissolved in methanol/dichloromethane and applied to an SCX column eluting with methanol and then a mixture of 0.880 ammonia/methanol (1:9). The basic fractions were combined and concentrated in vacuo to afford the title compound (65 mg, 70%); MS(ES+) m/e 368 [M+H]$^+$.

Step 6. 5-{2-Pyridin-4-yl-5-[4-(2-pyrrolidin-1-ylethoxy)phenyl]furan-3-yl}-indan-1-one A solution of the product from Step 5 (0.18 g, 0.47 mmol) in dimethylformamide (3 ml) was treated at 0° C. with sodium hydride (0.021 g of a 60% suspension in mineral oil, 0.52 mmol). The reaction mixture was stirred at 0° C. for 10 minutes and treated with another portion of sodium hydride (0.021 g of a 60% suspension in mineral oil, 0.52 mmol) and 1-(2-chloroethyl)pyrrolidine hydrochloride salt (0.088 g, 0.52 mmol) and stirred at room temperature overnight. The reaction mixture was poured onto aqueous sodium bicarbonate solution and the mixture was applied to an SCX column eluting with methanol followed by a mixture of 0.880 ammonia/methanol (1:9). The basic fractions were combined and concentrated in vacuo. The residue was chromatographed on silica gel eluting with 0.880 ammonia/methanol/dichloromethane (0.5:4.5:95) to afford the title compound (0.081 mg, 36%); MS(ES+) m/e 465 [M+H]$^+$.

Step 7. 5-{2-Pyridin-4-yl-5-[4-(2-pyrrolidin-1-ylethoxy)phenyl]-furan-3-yl}indan-1-one oxime The title compound was prepared from the product of Step 6 using the method of Example 1 Step 7; MS(ES+) m/e 480 [M+H]$^+$.

EXAMPLE 13

5-{5-[4-(Piperidin-4-yloxy)phenyl]-2-pyridin-4-ylfuran-3-yl}indan-1-one oxime

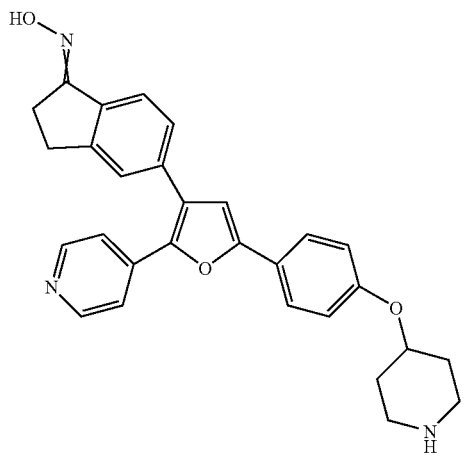

Step 1. 4-(4-Acetylphenoxy)piperidine-1-carboxylic acid tert-butyl ester

A solution of 1-(4-hydroxyphenyl)ethanone (1.48 g, 10.9 mmol) and tributylphosphine (3.0 g, 14.9 mmol) in toluene (20 ml) was treated dropwise at 0° C. with a solution of 4-hydroxypiperidine-1-carboxylic acid tert-butyl ester (2 g, 9.94 mmol) and 1,1'-(azodicarbonyl)dipiperidine (2.75 g, 10.9 mmol) in toluene (20 ml). The mixture was stirred at room temperature for 2 days then partitioned between aqueous sodium bicarbonate solution and dichloromethane. The organic layer was dried ($MgSO_4$) and concentrated in vacuo. The residue was chromatographed on silica gel eluting with a mixture of methanol/dichloromethane (1:9) to afford the title compound (0.81 g, 23%); MS(ES−) m/e 318 [M−H]$^-$.

Step 2. 4-{4-[(E)-3-(1-Methoxyimino-indan-5-yl)allanoyl]phenoxy}piperidine-1-carboxylic acid tert-butyl ester The title compound (0.9 g, 75%) was prepared from the product of Step 1 and the product of Example 1 Step 2 using the method of Example 2 Step 1. $^1$H NMR (CDCl$_3$) 8.03 (2H, d, J 8.8 Hz), 7.80 (1H, d, J 15.6 Hz), 7.72 (1H, d, J 8.4 Hz), 7.56 (3H, m), 6.98 (2H, d J 8.8 Hz), 4.6 (1H, m), 4.01 (3H, s), 3.70 (2H, m), 3.35 (2H, m), 3.07 (2H, m), 2.92 (2H, m), 1.95 (2H, m), 1.80 (2H,m), 1.47 (9H, s).

Step 3. 4-{4-[3-(1-Methoxyiminoindan-5-yl)4-oxo-4-pyridin-4-ylbutanoyl]phenoxy}piperidine-1-carboxylic acid tert-butyl ester The title compound (0.9 g, 88%) was prepared from the product of Step 2 and pyridine-4-carboxaldehyde using the method of Example 1 Step 4; MS(ES+) m/e 597 [M+H]+.

Step 4. 5-{5-[4-(Piperidin4-yloxy)phenyl]-2-pyridin-4-ylfuran-3-yl}indan-1-one O-methyloxime The title compound (140 mg, 40%) was prepared from the product of Step 3 using the method of Example 3 Step 1; MS(ES+) m/e 480 [M+H]+.

Step 5. 5-{5-[4-(Piperidin-4-yloxy)phenyl]-2-pyridin-4-ylfuran-3-yl}indan-1-one oxime The title compound (47 mg, 67%) was prepared from the product of Step 4 using the method of Example 1 Steps 6 and 7; MS(ES+) m/e 466 [M+H]+.

EXAMPLE 14

5(2-Pyridin-4-ylfuran-3-yl)indan-1-one oxime

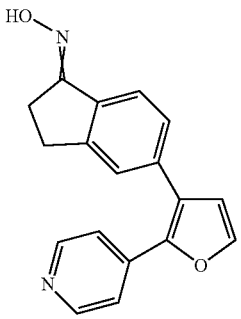

Step 1. 5-(2-Pyridin-4-ylfuran-3-yl)indan-1-one

A solution of the product of Example 5 Step 5 (0.22 g, 1 mmol), 5-(4,4,5,5-tetramethyl-[1,3,2]-dioxaborolan-2-yl)indanone (0.25 g, 1 mmol) (WO98/45265) and potassium acetate (294 mg, 3 mmol) in dimethylformamide (2 ml), ethanol (2 ml) and water (2 ml) was treated with palladium (II) acetate (12 mg, 0.05 mmol) and triphenylphosphine (26.2 mg, 0.1 mmol) and heated under reflux for 5 hours. The reaction mixture was cooled to room temperature filtered through celite and concentrated in vacuo. The residue was diluted with ethyl acetate, washed with water and saturated brine, dried (MgSO$_4$) and concentrated in vacuo. The residue was chromatographed on silica gel eluting with hexane/ethyl acetate (1:1) and methanol/ethyl acetate (1:9) to afford the title compound (0.17 g, 62%); MS(ES+) m/e 276 [M+H]+.

Step 2. 5-(2-Pyridin-4-ylfuran-3-yl)indan-1-one oxime

The title compound (30 mg, 52%) was prepared from the product of Step 1 using the method of Example 1 Step 7; MS(ES+) m/e 291 [M+H]+.

EXAMPLE 15

5-[2-(2-Aminopyrimidin-4-yl)furan-3-yl]indan-1-one oxime

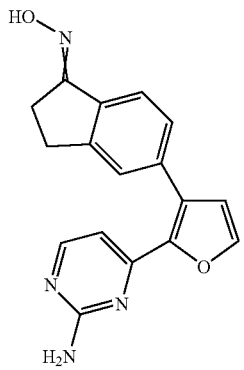

Step 1. 5-(2-Acetylfuran-3-yl)indan-1-one O-methyloxime

A mixture of 1-(3-bromofuran-2-yl)ethanone (A. Tanaka et al., J. Heterocycl. Chem., 1995, 32, 4 1289) (2.5 g, 13.2 mmol), the product of Example 5 Step 6 (2.83 g, 13.9 mmol), sodium carbonate (2.8 g, 27.7 mmol) in toluene (40 ml) and water (14 ml) was treated with triphenylphosphine (0.35 g, 1.3 mmol) and palladium acetate (150 mg, 0.66 mmol) and heated under reflux for 18 hours. After cooling to room temperature, the mixture was filtered through celite and the filtrate diluted with water and ethyl acetate. The organic phase was separated, washed with water and saturated brine, dried (MgSO$_4$), concentrated in vacuo and the residue chromatographed on silica gel eluting with a mixture of diethyl ether/dichloromethane (5:95) to afford the title compound (2.5 g, 70%); MS(ES+) m/e 270 [M+H]+.

Step 2: 5-[2-((E)-3-Dimethylaminoallanoyl)furan-3-yl]indan-1-one O-methyloxime

A solution of the product of Step 1 (0.15 g, 0.56 mmol) in N,N-dimethylformamide dimethyl acetal (5 ml) was heated at 100° C. for 18 hours. After cooling to room temperature, the solvent was removed in vacuo to afford the title compound (0.18 g, 98%); MS (ES+) m/e 325 [M+H]+.

Step 3. 5-[2-(2-Aminopyrimidin-4-yl)furan-3-yl]indan-1-one O-methyloxime

A solution of the product of Step 2 (0.30 g, 0.93 mmol) in 1,4dioxane (6 ml) was treated with a solution of guanidine carbonate (0.33 g, 1.86 mmol) and sodium hydroxide (0.1 7 g, 4.1 mmol) in water (2 ml). The mixture was heated at 100° C. for 4 hours. After cooling to room temperature, water was added and the mixture extracted into ethyl acetate (2×). The organic layers were combined and washed with saturated brine, dried (MgSO$_4$) and concentrated in vacuo. The residue was triturated with dichloromethane and the resulting solid filtered to afford the title compound (200 mg, 67%); MS(ES+) m/e 321 [M+H]+.

Step 4. 5-[2-(2-Aminopyrimidin-4-yl)furan-3-yl]indan-1-one oxime

The title compound (33 mg, 64%) was prepared from the product of Step 4 using the method of Example 1 Steps 6 and 7; MS(ES+) m/e 307 [M+H]+.

EXAMPLE 16

5-[3-(2-Aminopyrimidin-4-yl)furan-2-yl]-indan-1-one oxime

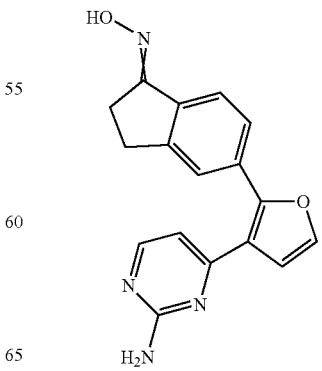

Step 1. 5-(3-Bromofuran-2-yl)indan-1-one O-methyloxime

The title compound (1.6 g, 30%) was prepared from 2,3-dibromofuran and the product of Example 5 Step 6 using the method of Example 15 Step 1; $^1$H NMR (CDCl$_3$) 7.88 (2H, m), 7.72 (1H, d, J 8.3 Hz), 7.42 (2H, d, J 3.1 Hz), 4.01 (3H, s), 3.17 (2H, m), 2.92 (2H, m).

Step 2. 5-(3-Acetylfuran-2-yl)indan-1-one O-methyloxime

The title compound (0.70 g, 57%) was prepared from the product of Step 1 using the method of Example 7 Step 1: $^1$H NMR (CDCl$_3$) 7.91 (1H, s), 7.80 (2H, m), 7.45 (1H, d, J 2.0 Hz), 6.80 (1H, d, J 2.0 Hz), 4.00 (3H, s), 3.07 (2H, m), 2.92 (2H, m), 2.44 (3H, s).

Step 3. 5-[3-(2-Aminopyrimidin-4-yl)furan-2-yl]indan-1-one oxime

The title compound was prepared from the product of Step 2 (0.30 g, 0.62 mmol) using the procedures described in Example 15 Steps 2-4; MS(ES−) m/e 306 [M−H]$^-$.

It is to be understood that the present invention covers all combinations of particular and preferred subgroups described hereinabove.

BIOLOGICAL EXAMPLES

The activity of compounds of formula (I) as B-Raf inhibitors may be determined by the following in vitro assay:

Fluorescence Anisotropy Kinase Binding Assay

The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10×Ki) of a potent inhibitor the anisotropy of the unbound fluorescent ligand is measurably different from the bound value.

The concentration of kinase enzyme should preferably be ≧1×K$_f$. The concentration of fluorescent ligand required will depend on the instrumentation used, and the fluorescent and physicochemical properties. The concentration used must be lower than the concentration of kinase enzyme, and preferably less than half the kinase enzyme concentration. A typical protocol is:

All compounds are serially diluted in DMSO, then by a one step dilution into buffer of comparison, 50 mM HEPES, pharmaceutical pH7.5, 1 mM CHAPS, 10 mM MgCL$_2$, for the assay.

B-Raf Enzyme concentration: 1 nM
Fluorescent ligand concentration: 0.5 nM
Test compound concentration: 0.5 nM -100 uM Components incubated in 10 ul final volume in LJL HE 384 type B black microtitre plate until equilibrium reached (Over 3 h, up to 30 h)

Fluorescence anisotropy read in an LJL Acquest.

Definitions:
Ki=dissociation constant for inhibitor binding
Kf=dissociation constant for fluorescent ligand binding The fluorescent ligand is the following compound:

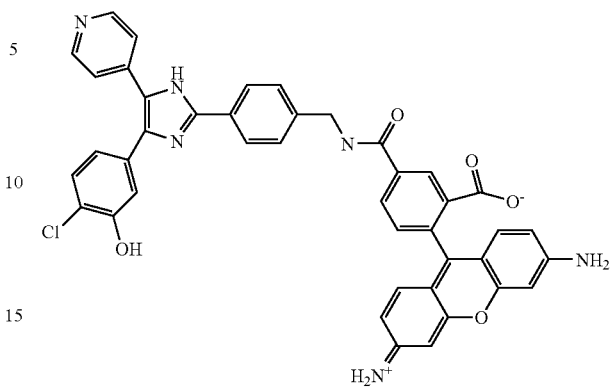

which is derived from 5-[2-(4-aminomethylphenyl)-5-pyridin-4-yl]-1H-imidazol4-yl]-2-chlorophenol and rhodamine green.

Compounds of the invention have a K$_d$ of less than 1 μM.

Raf Kinase Assay

Activity of human recombinant B-Raf protein was assessed in vitro by assay of the incorporation of radiolabelled phosphate to recombinant MAP kinase kinase (MEK), a known physiologic substrate of B-Raf. Catalytically active human recombinant B-Raf protein was obtained by purification from Sf9 insect cells infected with a human B-Raf recombinant baculovirus expression vector. To ensure that all substrate phosphorylation resulted from B-Raf activity, a catalytically inactive form of MEK was utilised. This protein was purified from bacterial cells expressing mutant inactive MEK as a fusion protein with glutathione-S-transferase (GST-kdMEK).

Method: Standard assay conditions of B-Raf catalytic activity utilised 3 ug of GST-kdMEK, 10 uM ATP and 2 uCi $^{33}$P-ATP, 50 mM MOPS, 0.1 mM EDTA, 0.1M sucrose, 10 mM MgCl$_2$ plus 0.1% dimethylsulphoxide (containing compound where appropriate) in a total reaction volume of 30 ul. Reactions were incubated at 25° C. for 90 minutes and reactions terminated by addition of EDTA to a final concentration of 50 uM. 10 ul of reaction was spotted to P81 phosphocellulose paper and air dried. Following four washes in ice cold 10% trichloroacetic acid, 0.5% phosphoric acid, papers were air dried prior to addition of liquid scintillant and measurement of radioactvity in a scintillation counter.

Results: The compounds of the examples were found to be effective in inhibiting B-Raf mediated phosphorylation of GST-kdMEK substrate having IC$_{50}$'s of <3 μM.

The activity of compounds as Raf inhibitors may also be determined by the assays described in WO 99/10325; McDonald, O. B., Chen, W. J., Ellis, B., Hoffman, C., Overton, L., Rink, M., Smith, A., Marshall, C. J. and Wood, E. R. (1999) A scintillation proximity assay for the Raf/MEK/ERK kinase cascade: high throughput screening and identification of selective enzyme inhibitors, Anal. Biochem. 268: 318-329 and AACR meeting New Orleans 1998 Poster 3793.

The neuroprotective properties of B-Raf inhibitors may be determined by the following in vitro assay:

Neuroprotective Properties of B-Raf Inhibitors in Rat Hippocampal Slice Cultures Organotypic cultures provide an intermediate between dissociated neuronal cell cultures and in-vivo models of oxygen and glucose deprivation (OGD). The majority of glial-neuronal interactions and neuronal circuitry are maintained in cultured hippocampal slices, so facilitating investigation of the patterns of death among differing cell types in a model that resembles the in vivo situation. These cultures allow the study of delayed cellular damage and death 24 hours, or more, post-insult and permit assessment of the consequences of long-term alterations in culture conditions. A number of laboratories have reported delayed neuronal damage in response to OGD in organotypic cultures of the hippocampus (Vornov et al., Stroke, 1994, 25, 57-465; Newell et al., Brain Res., 1995, 676, 3844). Several classes of compounds have been shown to protect in this model, including EAA antagonists (Strasser et al., Brain Res., 1995, 687, 167-174), Na channel blockers (Tasker et al., J. Neurosci., 1992, 12, 984308) and Ca channel blockers (Pringle et al., Stroke, 1996, 7, 2124-2130). To date, relatively little is known of the roles of intracellular kinase mediated signalling pathways in neuronal cell death in this model.

Method: Organotypic hippocampal slice cultures were prepared using the method of Stoppini et al., J. Neurosci. Methods, 1995, 37, 173-182. Briefly, 400 micron sections prepared from hippocampi of 7-8 day postnatal Sprague Dawley rats are cultured on semiporous membranes for 9-12 days. OGD is then induced by incubation in serum and glucose-free medium in an anaerobic chamber for 45 minutes. Cultures are then returned to the air/$CO_2$ incubator for 23 hours before analysis. Propidium iodide (PI) is used as an indicator of cell death. PI is non toxic to neurones and has been used in many studies to ascertain cell viability. In damaged neurons PI enters and binds to nucleic acids. Bound PI shows increased emission at 635 nm when excited at 540 nm. One PI fluorescence image and one white light image are taken and the proportion of cell death analysed. The area of region CA1 is defined from the white light image and superimposed over the PI image. The PI signal is thresholded and area of PI damage expressed as a percentage of the CA1 area. Correlation between PI fluorescence and histologically confirmed cell death has been validated previously by Niss1-staining using cresyl fast violet (Newell et al., J. Neurosci., 1995, 15, 7702-7711).

Methylene Blue Growth Inhibition Assay (Assay 2)

Normal human foreskin fibroblasts (HFF), human melanoma (A375P, SKMEL2, SKMEL3) colon carcinoma (Colo 205) were cultured in the following growth media: A375P, Colo 205, Roswell Park Memorial Institute (RPMI) 1640 (Life Technologies 22400-089) containing 10% fetal bovine serum (FBS); HFF, Dulbecco's modified Eagle Medium (DMEM) (Life Technologies 12320-032) containing 10% FBS; SKMEL2 and SKMEL3, Minimum Essential Medium (MEM, Life Technologies 11095-080) containing 1X non-essential amino acids (Life Technologies 11140-050) and 10% FBS. Cells were harvested using 0.25%trypsin/1 mM, EDTA, counted using a haemocytometer, and plated in 100 microliters of the appropriate media, at the following densities, in a 96-well tissue culture plate (Falcon 3075): HFF and A375P, 5,000 cells/well; all other cell lines, 10,000 cells/well. The next day, compounds were diluted in RPMI containing 100 micrograms/ml gentamicin, at twice the final required concentration, from 10 mM stock solutions in dimethyl sulphoxide (DMSO). One hundred microliters per well of these dilutions were added to the 100 microliters of media currently on the cell plates. RPMI containing 0.6% DMSO was added to control wells. Compounds diluted in. The final concentration of DMSO in all wells was 0.3%. Cells were incubated at 37° C., 5% $CO_2$ for 3 days. Medium was removed by aspiration. Cell biomass was estimated by staining cells with 90 µl per well methylene blue (Sigma M9140, 0.5% in 50:50 ethanol:water) and incubation at room temperature for at least 30 minutes. Stain was removed, the plates rinsed by immersion in deionized water and air-dried. To release stain from the cells 100 µl of solubilization solution was added (1% N-lauroyl sarcosine, sodium salt, Sigma L5125, in phosphate-buffered saline solution (PBS)), and plates were incubated at room temperature for 30 minutes. Optical density at 620 nM was measured on a microplate reader. Percent inhibition of cell growth was calculated relative to vehicle treated control wells. Concentration of compound that inhibits 50% of cell growth ($IC_{50}$) was interpolated using nonlinear regression (Levenberg-Marquardt) and the equation, $y=V_{max}*(1-(x/(K+x)))+Y2$, where "K" was equal to the $IC_{50}$.

XTT 72 hr Growth Inhibition Protocol for Mammalian Cultured Cells (Assay 3)

Human diploid foreskin fibroblasts (HFF) or human colon carcinoma (Colo 201) cells were grown in Dulbecco's modified Eagle's medium (DMEM) (Invitrogen/Life Technologies) containing 10% fetal bovine serum (FBS) and the antibiotics penicillin (100 Units/ml) and streotomycin (100 micrograms/ml) (Invitrogen/Life Technologies). Growth was at 37° C. in humidified 5% CO2 incubators in 75 $cm^2$ plastic flasks. Cells were harvested using 0.25% trypsin/1 mM ethylenediaminetetraacetic acid (EDTA), resuspended in growth medium, and counted using a hemocytometer. Flat-bottomed 96-well plates were seeded with $2\times10^3$ cells/well in a volume of 200 ul from trypsinized exponentially growing cultures. To "blank" wells, growth medium was added with no additions. Cells were incubated overnight to permit attachment.

Next day, medium from wells that contained cells was replaced with 180 microliters of fresh medium. Appropriate dilutions of test compounds were added to the wells from stock soloutions of compound dissolved in dimethyl sulfoxide (DMSO); final DMSO concentration in all wells was 0.2%. Cells plus compound were incubated for an additional 72 hr at 37° C. under normal growth conditions. Cells were then assayed for viability using standard XTT/PMS*. Fifty microliters of XTT/PMS solution was added to each well and plates were incubated for 90 minutes at 37° C. Absorbance at 450 nM was then determined using a 96-well UV plate reader (Molecular Devices). Under these conditions, absorbance of untreated control cells at 450 nm was at least 1.0 optical density unit/ml. Percent viability of cells in each well was calculated from these data (having been corrected for background absorbance). It was equal to 100×(A450 test well/A450 untreated control well), the A450s being averages of triplicate determinations. IC50 was that concentration of compound that reduced cell viability to 50% of control (untreated) viability, as determined from plots of concentration vs percent viability.

Preparation of XTT/PMS Solution (immediately before assay).

For each 96-well plate, 8 mg XTT (2,3-bis[2-Methoxy4-nitro-5-sulfophenyl]-2H-tetrazolium-5-carboxanilide) (Sigma Chemical Co.) per plate was dissolved in 100 ul DMSO. 3.9 ml $H_2O$ was added to dissolve XTT and 20 ul of PMS (phenazine methosulfate, Sigma Chemical Co.) stock solution (30 mg/ml) was added from frozen aliquoted stock solution (10 mg of PMS in 3.3 ml phosphate buffered saline (Invitrogen/Life Technologies). (These stocks are routinely frozen at −20° C. until use).

Normal human foreskin fibroblasts (HFF) are the control normal cell line that should not be inhibited or at least much less sensitive.

| | | Cell Line | HFF | Colo201 | Colo205 | A375P | SKMEL3 | SKMEL2 |
|---|---|---|---|---|---|---|---|---|
| | | Pathology | normal | Colorectal cancer | Colorectal cancer | melanoma | melanoma | melanoma |
| | | B-Raf Status | wt | ND | V599E | V599E | V599E | wt |
| | B-Raf, nM Kd | Ras Status | wt | ND | wt | wt | wt | [Q6IR]N-Ras |
| Example No | Assay 1 | | | Assay 3 | Assay 3 | Assay 2 | Assay 2 | Assay 2 | Assay 2 |
| 4 | 1.0 | | | 7.1* | 0.5△ | 0.11† | 0.081† | 1.0△ | 0.22† |

*indicates IC50 > 3 μM
△indicates IC50 0.3-3 μM
†indicates IC50 < 0.3 μM

A375, Colo205 and SKMEL are reported as wild type (wt) for Ras status in the literature.

V599E indicates that the cell lines have activating BRaf mutation (V599E)

ND represents not determined

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part may be used as a basis for priority in respect of any subsequent application. The claims of such subsequent application may be directed to any feature or combination of features described herein. They may take the form of composition, process, or use claims and may include by way of example and without limitation the following claims.

The invention claimed is:

1. A compound of formula (I):

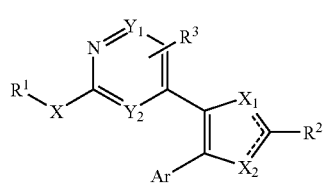

wherein:

X is O, $CH_2$, CO, S or NH, or the moiety $X-R^1$ is hydrogen;

$Y_1$ and $Y_2$ independently represent CH or N;

$R^1$ is hydrogen, $C_{1-6}$alkyl, $C_{3-7}$cycloalkyl, aryl, aryl$C_{1-6}$alkyl-, heterocyclyl, heterocyclyl$C_{1-6}$alkyl-, heteroaryl, or heteroaryl$C_{1-6}$alkyl-, any of which, except hydrogen, may be optionally substituted;

$R^2$ is hydrogen or an optionally substituted aryl or heteroaryl group;

Ar is a group of the formula a) or b):

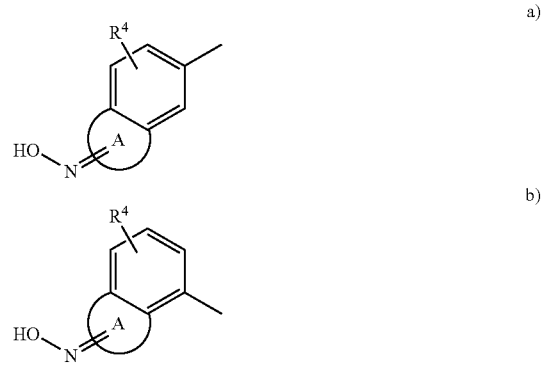

wherein A represents a fused 5- to 7-membered ring optionally containing up to two heteroatoms selected from O, S and $NR^5$, wherein $R^5$ is hydrogen or $C_{1-6}$alkyl, which ring is optionally substituted by up to 2 substituents selected from halogen, $C_{1-6}$alkyl, hydroxy, $C_{1-6}$alkoxy or keto;

$R^3$ and $R^4$ are independently selected from hydrogen, halogen, $C_{1-6}$alkyl, aryl, aryl$C_{1-6}$alkyl, $C_{1-6}$alkoxy, $C_{1-6}$alkoxy$C_{1-6}$alkyl, halo$C_{1-6}$alkyl, aryl$C_{1-6}$alkoxy, hydroxy, nitro, cyano, azido, amino, mono- and di-N—$C_{1-6}$alkylamino, acylamino, arylcarbonylamino, acyloxy, carboxy, carboxy salts, carboxy esters, carbamoyl, mono- and di-N—$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkyl sulphinyl or $C_{1-6}$alkylsulphonyl; and one of $X_1$ and $X_2$ is selected from O, S or $NR^{11}$ and the other is CH, wherein $R^{11}$ is hydrogen, $C_{1-6}$alkyl, aryl or aryl$C_{1-6}$alkyl;

or a pharmaceutically acceptable salt thereof.

2. The compound according to claim 1, wherein $X-R^1$ is hydrogen.

3. The compound according to claim 1, wherein A represents a fused 5 membered ring optionally containing up to two heteroatoms selected from O, S and $NR^5$, wherein $R^5$ is hydrogen or $C_{1-6}$alkyl, which ring is optionally substituted by up to 2 substituents selected from halogen, $C_{1-6}$alkyl, hydroxy, $C_{1-6}$alkoxy or keto.

4. The compound according to claim 1, wherein $R^2$ is hydrogen or an optionally substituted phenyl or pyrimidinyl.

5. The compound according to claim 1, wherein $X_1$ or $X_2$ are O.

6. A compound, wherein the compound is selected from:
- 5-{5-[4-(2-Dimethylaminoethoxy)phenyl]-3-pyridin-4-yl-1H-pyrrol-2-yl}indan-1-one oxime;
- 5-{5-[4-(2-Dimethylaminoethoxy)phenyl]-2-pyridin-4-yl-1H-pyrrol-3-yl}indan-1-one oxime;
- 5-{5-[4-(2-Dimethylaminoethoxy)phenyl]-3-pyridin-4-ylfuran-2-yl}indan-1-one oxime;
- 5-{5-[4-(2-Dimethylaminoethoxy)phenyl]-2-pyridin-4-yl-furan-3-yl}indan-1-one oxime;
- 5-{5-[2-(2-Dimethylaminoethoxy)pyrimidin-5-yl]-2-pyridin-4-ylfuran-3-yl}indan-1-one oxime;
- 5-{5-[2-(2-Morpholin-4-ylethoxy)pyrimidin-5-yl]-2-pyridin-4-ylfuran-3-yl}indan-1-one oxime;
- 5-{5-[2-(4-Methylpiperazin-1-yl)pyrimidin-5-yl]-2-pyridin-4-ylfuran-3-yl}indan-1-one oxime;
- 5-[5-(2-Piperazin-1-ylpyrimidin-5-yl)-2-pyridin-4-ylfuran-3-yl]indan-1-one oxime;
- 5-{5-[2-(2-Dimethylaminoethylamino)pyrimidin-5-yl]-2-pyridin-4-yl-furan-3-yl}indan-1-one oxime;
- 5-{5-[4-(2-Dimethylaminoethoxy)phenyl]-3-(2-methylpyridin-4-yl-furan-2-yl}indan-1-one oxime;
- 5-{2-(2-Aminopyrimidin-4-yl)-5-[4-(2-dimethylaminoethoxy)phenyl]furan-3-yl}indan-1-one oxime;
- 5-{2-Pyridin-4-yl-5-[4-(2-pyrrolidin-1-ylethoxy)phenyl]furan-3-yl}indan-1-one oxime;
- 5-{5-[4-(Piperidin-4-yloxy)phenyl]-2-pyridin-4-ylfuran-3-yl}indan-1-one oxime;
- 5-(2-Pyridin-4-ylfuran-3-yl)indan-1-one oxime;
- 5-[2-(2-Aminopyrimidin-4-yl)furan-3-yl]indan-1-one oxime; and
- 5-[3-(2-Aminopyrimidin-4-yl)furan-2-yl]-indan-1-one oxime.

7. A pharmaceutical composition comprising a compound according to claim 1 or a pharmaceutically acceptable salt thereof and a pharmaceutically acceptable carrier.

8. A method for therapeutic treatment of colorectal cancer in a human, or other mammal, which comprises administering a therapeutically effective amount of a compound of claim 1 of formula (I) or a pharmaceutically acceptable salt thereof.

9. A method for therapeutic treatment of melanoma in a human, or other mammal, which comprises administering a therapeutically effective amount of a compound of claim 1 of formula (I) or a pharmaceutically acceptable salt thereof.

* * * * *